United States Patent [19]

Jensen et al.

[11] Patent Number: 6,114,120

[45] Date of Patent: *Sep. 5, 2000

[54] SYSTEMATIC EVOLUTION OF LIGANDS BY EXPONENTIAL ENRICHMENT: TISSUE SELEX

[75] Inventors: Kirk B Jensen, New York, N.Y.; Hang Chen, San Francisco, Calif.; Kevin N. Morris, Goldegg, Austria; Andrew Stephens; Larry Gold, both of Boulder, Colo.

[73] Assignee: NeXstar Pharmaceuticals, Inc., Boulder, Colo.

[ * ] Notice: This patent is subject to a terminal disclaimer.

[21] Appl. No.: 08/945,909

[22] PCT Filed: May 1, 1996

[86] PCT No.: PCT/US96/06060

§ 371 Date: Oct. 28, 1997

§ 102(e) Date: Oct. 28, 1997

[87] PCT Pub. No.: WO96/34875

PCT Pub. Date: Nov. 7, 1996

Related U.S. Application Data

[63] Continuation-in-part of application No. 08/434,425, May 3, 1995, Pat. No. 5,789,157, and a continuation-in-part of application No. 08/437,667, May 3, 1995, Pat. No. 5,864,026, and a continuation-in-part of application No. 08/434,001, May 3, 1995, Pat. No. 5,712,375, and a continuation-in-part of application No. 08/433,585, May 3, 1995, Pat. No. 5,763,566.

[51] Int. Cl.⁷ .......................... C07H 21/02; C07H 21/04; C12P 19/34; C12Q 1/68
[52] U.S. Cl. ............................ 435/6; 435/91.2; 536/22.1; 536/24.3; 536/25.4
[58] Field of Search .................... 435/6, 91.2; 536/22.1, 536/23.1, 25.4, 24.3; 935/77.78

[56] References Cited

U.S. PATENT DOCUMENTS

| | | | |
|---|---|---|---|
| 5,270,163 | 12/1993 | Gold et al. | 435/6 |
| 5,475,096 | 12/1995 | Gold et al. | 435/6 |
| 5,688,935 | 11/1997 | Stephens et al. | 536/23.1 |
| 5,712,375 | 1/1998 | Jensen et al. | 530/412 |
| 5,750,342 | 5/1998 | Stephens et al. | 435/6 |
| 5,763,566 | 6/1998 | Jensen et al. | 530/350 |

FOREIGN PATENT DOCUMENTS

| | | |
|---|---|---|
| 2 183 661 | 6/1987 | United Kingdom . |
| WO89/06694 | 7/1989 | WIPO . |
| WO 91/14843 | 9/1992 | WIPO ........................................ 435/6 |
| WO92/14843 | 9/1992 | WIPO . |
| WO 94/06934 | 3/1994 | WIPO . |

OTHER PUBLICATIONS

Joyce (1989) Gene 82:83.
Joyce & Inoue (1989) Nucleic Acids Research 17:711.
Ellington & Szostak (1990) Abstracts of papers presented at the 1990 meeting on RNA Processing, Cold Spring Harbor Laboratory, Cold Spring Harbor, NY, p. 84.
Kinzler & Vogelstein (1989) Nucleic Acids Research 17:3645.
Kramer et al. (1974) J. Mol. Biol. 89:719.
Levisohn & Spiegelman (1969) PNAS USA 63:805.
Levisohn & Spiegelman (1968) PNAS USA 60:866.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Thiesen & Bach (1990) Nucleic Acids Research 18:3203.
Tsai and Keene (1993) J. Immunol. 150:1137.
Benjamini and Leskowitz (1988) Immunology: A Short Course, Alan R. Liss, Inc., NY, NY p. 36.
Rosenfeld et al. (1986) J. Biol. Chem. 261:1398.
Gath et al. (1996) *Biology and Physiology of the Blood Brain Barrier*, Courand and Scherman eds., Chapter 25, pp. 153–158.
Dehouck et al. (1996) *Biology and Physiology of the Blood Brain Barrier*, Courand and Scherman eds., Chapter 23, pp. 143–146.
Dehouck et al. (1990) Journal of Neurochemistry 54:1798.

*Primary Examiner*—Stephanie Zitomer
*Attorney, Agent, or Firm*—Swanson & Bratschun LLC

[57] ABSTRACT

A new class of nucleic acid compounds, referred to as nucleic acid ligands, have been shown to exist that have a specific binding affinity for three dimensional molecular targets, including cell surface macromolecules. The nucleic acid ligands are identified by the method of the invention referred to as the Systematic Evolution of Ligands by EXponential enrichment (SELEX), wherein a candidate mixture of nucleic acids are iteratively enriched and the high affinity nucleic acids are amplified for further partitioning. The high affinity nucleic acid ligands are useful in capturing target cells.

10 Claims, 7 Drawing Sheets

Motif I c56t
5' a a c t c a g t g g t a g g t a a c g g t t 3'  SEQ ID NO:4 c20t
5' a a c t c a g t a a t g c c a a g g t a a c g g t t 3'  SEQ ID NO:236

FIGURE 3A

Motif II

```
    c16t              c79t c   g             c   g
    a     t           c     t
     a - t             a - t
     c - g             c - g
     c • c             c • t
     c • c             c • c
     g - c             g - c
     t - a             t - a
     t - a             t - a
    a    |            g    |
   c     |           a     |
    g    |            t    |
     c - g             a - t
     t - a             a - t
     a - t             c - g
     a - t             t - a
     g - c             c - g
     c - g             g - c
    5'   3'            c - g
                      5'   3'

SEQ ID NO:237    SEQ ID NO:238
```

FIGURE 3B

```
         g g t
       t       c
    t               t         c111t
    t               t
      c                 t c g a c  3'
       c                | | | | |
         a              a g c t g  5'
            a        g          SEQ ID NO:239
              c - g
              g - c
              t   a
                t           Motif III
```

```
         a g t
       g       a
    t               t         c53t
    t               t              c
      c                 t c a t g    t
       c                | | | | |     t
         a              a g t a c    c
            a        g              a g
              c - g
              g - c
              g - c
              g - c
              5'  3'        SEQ ID NO:240
```

FIGURE 3C

SYSTEMATIC EVOLUTION OF LIGANDS BY EXPONENTIAL ENRICHMENT: TISSUE SELEX

This application is a 35 USC §371 national application of PCT/US96/06060, filed May 1, 1996, a continuation-in-part of Ser. No. 08/434,425, filed May 3, 1995, now U.S. Pat. No. 5,789,157, a continuation-in-part of Ser. No. 08/437,667, filed May 3, 1995, now U.S. Pat. No. 5,864,026, a continuation-in-part of Ser. No. 08/434,001, filed May 3, 1995, now U.S. Pat. No. 5,712,375, and a continuation-in-part of Ser. No. 08/433,585, filed May 3, 1995, now U.S. Pat. No. 5,763,566.

This work was supported by grants from the United States Government funded through the National Institutes of Health. The U.S. Government has certain rights to this invention.

FIELD OF THE INVENTION

Described herein are methods for identifying and preparing nucleic acid ligands to tissues. Tissues are described herein as a collection of macromolecules in a heterogeneous environment. According to this definition, tissues encompass a single cell type, a collection of cell types, an aggregate of cells or an aggregate of macromolecules. The method utilized herein for identifying such nucleic acid ligands is called SELEX, an acronym for Systematic Evolution of Ligands by EXponential enrichment. Specifically disclosed herein are high-affinity nucleic acid ligands which bind to various tissues.

BACKGROUND OF THE INVENTION

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment", now abandoned, U.S. patent application Ser. No. 07/714,131, filed Jun. 10, 1991, entitled "Nucleic Acid Ligands now U.S. Pat. No. 5,475,096, U.S. patent application Ser. No. 07/931,473, filed Aug. 17, 1992, entitled "Nucleic Acid Ligands", now U.S. Pat. No. 5,270,163 (see also PCT/US91/04078), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure" describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands" now abandoned, describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine", describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX", describes a SELEX-based method which achieves highly efficient partitioning between oligonucleotides having high and low affinity for a target molecule. U.S. patent application Ser. No. 07/964,624, filed Oct. 21, 1992, entitled "Methods of Producing Nucleic Acid Ligands" describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX", describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Pyrimidine by Intramolecular Nucleophilic Displacement", describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" and U.S. patent application Ser. No. 08/234,997, filed Apr. 28, 1994, entitled "Systematic Evolution of Ligands by Exponential Enrichment: Blended SELEX", respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

Without question, the SELEX process is very powerful. However, to date the process has been successfully demonstrated primarily with pure, simple demonstration that complex targets are also compatible with the SELEX process. Tissue SELEX allows one to obtain nucleic acid ligands to multiple targets simultaneously, and is analogous to performing individual SELEX experiments on all the discrete components of a particular tissue.

It is desirable to be able to obtain nucleic acid ligands to complex tissue targets for various reasons. First, tissue SELEX can be useful to obtain nucleic acid ligands when a distinct target is unknown but a general mode of action of the desired ligand is suggested. Second, tissue SELEX can be useful when nucleic acid ligands are desired based on functional results. Since whole tissues or cells can be used in the SELEX process, it is possible to select for nucleic acid ligands which produce a particular phenotype in the tissue or cell. Third, it can be desirable to obtain nucleic acid ligands to a complex tissue target when it is unclear which single target would be effective. It is also useful to obtain nucleic acid ligands to a complex tissue target if the purified target is unavailable or unstable in its purified form (i.e., a membrane protein). Tissue SELEX allows the potential generation of ligands to previously unknown targets, and may rival monoclonal antibodies as reagents for research, diagnostics and therapeutics.

BRIEF SUMMARY OF THE INVENTION

The present invention includes methods of identifying and producing nucleic acid ligands to complex targets such as tissues and the nucleic acid ligands so identified and produced. More particularly, nucleic acid ligands are provided that are capable of binding specifically to tissues which are macromolecules in a heterogeneous environment, such as whole cells or substructures thereof, aggregates of cells, collections of cells, aggregates of macromolecules and the like.

Further included in this invention is a method of identifying nucleic acid ligands to tissues comprising the steps of (a) preparing a candidate mixture of nucleic acids, (b) partitioning between members of said candidate mixture on the basis of affinity to tissue, and (c) amplifying the selected molecules to yield a mixture of nucleic acids enriched for nucleic acid sequences with a relatively high affinity for binding to tissue. Also included are nucleic acid ligands identified according to such method.

Another embodiment of the invention includes methods wherein a negative selection is performed in order to perfect the discrimination between subtle differences of similar tissue types. In this embodiment, the resulting ligands are specific not only for a particular tissue type, but can discriminate between subtly different tissues of the same type. For example, this method can discriminate between normal and abnormal tissue types, between induced and uninduced tissue types, etc.

In another embodiment of the invention, a method is provided for identifying previously unknown or uncharacterized epitopes which are components of a larger unknown macromolecule, on the tissue target. The ligands that are evolved by the present invention are capable of binding to previously unknown epitopes and the macromolecule which comprises the unknown epitope can then be identified by standard methods. For example, ligands can be evolved to a previously unknown protein found in the context of a complex tissue target. The ligand of the invention can be used to purify the protein away from the tissue target by standard protein purification and identification methods. These standard methods include affinity purification, microsequencing and cDNA databank searches. In this aspect, the newly identified epitopes which are components of a larger unknown macromolecule, such as new or previously uncharacterized proteins, are provided by the invention. These new epitopes and the macromolecule of which they are a component will be useful as diagnostic and therapeutic agents as well as the ligands that helped identify them.

More specifically, the present invention includes nucleic acid ligands to red blood cell ghosts, human tumor cell lines, such as a T-cell lymphoblast cell line, CEMss, and an adherent cell line, the glioma U-251, including those ligands listed in Tables 1 and 2. Also included are nucleic acid ligands to the above-described tissues that are substantially homologous to any of the given ligands and that have substantially the same ability to bind the above-described tissues. Further included in this invention are nucleic acid ligands to the above-described tissues that have substantially the same structural form as the ligands presented herein.

BRIEF DESCRIPTION OF THE FIGURES

FIGS. 3A–3C show predicted secondary structures of six ligands which are the result of the RBC ghost SELEX. The six sequences are derived from the motif I (FIG. 3A), II (FIG. 3B) and III (FIG. 3C) classes of sequences (two from each motif) are truncated to the smallest functional size, as based upon phylogenetic and computer folding algorithms. Base pairing with each molecule is predicted as based upon phylogenetic and computer folding algorithms. Notice that the two ligands from motif III share common primary and secondary structures, but are circularly permuted in relation to each other.

FIG. 5 shows the photoaffinity crosslinking obtained after 3 rounds of the enrichment process described above.

DETAILED DESCRIPTION OF THE INVENTION

Figure 1:
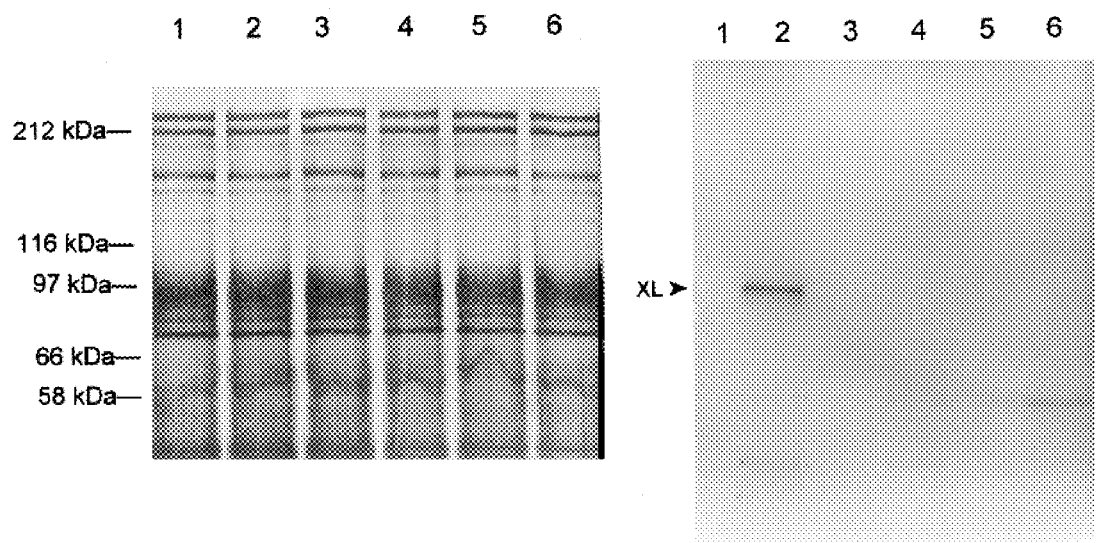
FIG. 1 shows the results of crosslinking a ligand to red blood cell ghosts [(c56t) (SEQ ID NO:4)] and nucleic acids of similar, but scrambled, sequences to red blood cell ghost membrane extracts. A distinct protein band is identified specifically by the ligand. Shown are a silver-stained 6% SDS gel and autoradiography of the same gel. Irradiations were performed with a hand-held transilluminator (254 nm) and samples were separated by gel electrophoesis under denaturing and reducing conditions. 1-0'irradiation c565 (SEQ ID NO:4); 2-5' irradiation c56t (SEQ ID NO:4); 3-0'irradiation scrambled oligo #1; 4-5'irradiation scrambled oligo #1; 5-0'irradiation scrambled oligo #2; 6-5'irradiation control oligo #2.

This application describes nucleic acid ligands to complex tissue targets identified generally according to the method known as the SELEX process. As stated earlier, the SELEX technology is described in detail, and incorporated herein by reference, in the SELEX Patent Applications. This method, referred to as the Tissue SELEX process, incorporates complex targets in contrast to the more simple targets previously used in the SELEX process. Certain terms used to describe the invention herein are defined as follows:

"SELEX" methodology refers to the combination of selection of nucleic acid ligands which interact with a target in a desirable manner, for example binding to a protein, with amplification of those selected nucleic acids as described in detail above and in the SELEX Patent Applications. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved.

"Tissue SELEX" methodology applies the SELEX methodology to tissue targets. Tissue SELEX has several advantages. First, using Tissue SELEX one can obtain ligands to specific cell types in the absence of a defined understanding of the involved epitope. The epitope against which a ligand is evolved in usually a substructural component of a larger macromolecule. The ligands found by this method could also be useful in identifying new proteins or other new macromolecules on the tissue target. The new proteins or other new macromolecules which comprise a newly identified epitope can be purified and characterized using standard procedures. Second, ligands can be obtained to defined epitopes or macromolecules in the context of their physiologic cellular or membrane environment. Examples of various tissue targets can include a membrane protein on a whole cell, a plasma protein in plasma, a nuclear protein in the presence of whole nuclear extracts, etc. Third, it is possible to obtain ligands to tissues in a functionally altered phenotype, e.g., activated, migrating, etc. The ligands and the new macromolecules containing the ligand epitopes identified by this process may be useful as diagnostics or therapeutics. Fourth, Tissue SELEX is a powerful methodology which allows one to identify nucleic acid ligands that can mediate many different cell behaviors, such as apoptosis, anergy, differentiation, proliferation, etc., without prior knowledge of the identity of the specific tissue targets that control these changes. The sensitivity of the SELEX process may lead to the generation of oligonucleotides that recognize potentially every different epitope on the complex tissue target. Larger numbers of different sequence motifs are expected using the tissue SELEX process, as compared with simple-target SELEX, since it is believed that different motifs will recognize distinct epitopes on the complex tissue target. Some epitopes may lie within the same protein, but many will be directed to various proteins or other molecules on the tissue. Tissue SELEX can be done in vivo or in vitro.

Tissue SELEX allows one to work with a complete living "element" (a cell or bigger) that allow one to phenotypically screen for a target-ligand interaction that effects this "element." For example, one could screen an evolved, high affinity tissue SELEX pool using flow cytometry for sequences which bind a membrane protein and cause the cell to carry out a biochemical transformation which is measured by the flow instrument.

Tissue SELEX allows one to obtain nucleic acid ligands to multiple targets simultaneously. All independent binding sites on a very large macromolecular complex such as a tissue or cell should be potential targets for selection. In effect, this allows one to take a tissue any carry out numerous SELEX procedures on this tissue that is theoretically equivalent to individual SELEXes on all individual components of the particular tissue.

In one embodiment, a negative selection process (termed counter-SELEX) is employed to enhance the possibility that the ligands derived by tissue SELEX have precise specificity and affinity. In this embodiment, ligands are selected for a specific tissue and then a negative selection is done against a related tissue which does not have certain characteristics for which the ligand is desired. The negative selection can be done against a similar cell line or cell type, different cells, normal tissue, plasma or blood, a non-specific antibody or other available ligand. An example of this negative selection would be to first select using a tumor cell target (such as a malignant melanoma) and then counterselect the resulting nucleic acids against a similar cell type which is not tumorogenic (such as normal human melanocytes). Ligands that interact with both normal and neoplastic tissue will be removed by this negative selection and only those nucleic acid ligands that specifically bind the tumor cells will be identified (or retained). The resulting nucleic acid ligand would be specific for tumors. This technique will provide the ability to identify nucleic acid ligands that can discriminate between two closely related targets, i.e., between a cancerous cell and an untransformed cell of the same tissue type. The negative selection can also be done in vivo. Using this method one can not only generate ligands to specific targets on complex tissue surfaces, but also be able to recognize the differences between normal and abnormal tissue of a particular type.

"SELEX Target" or "Target" refers to any compound upon which a nucleic acid can act in a predetermined desirable manner. A SELEX target molecule can be a protein, peptide, nucleic acid, carbohydrate, lipid, polysaccharide, glycoprotein, hormone, receptor, antigen, antibody, virus, pathogen, toxic substance, substrate metabolite, transition state analog, cofactor, inhibitor, drug, dye, nutrient, growth factor, cell, tissue, etc., without limitation. Virtually any chemical or biological effector would be a suitable SELEX target. Molecules of any size can serve as SELEX targets. A target can also be modified in certain ways to enhance the likelihood of an interaction between the target and the nucleic acid.

"Tissue target" or "Tissue" refers to a certain subset of the SELEX targets described above. According to this definition, tissues are macromolecules in a heterogeneous environment. As used herein, tissue refers to a single cell type, a collection of cell types, an aggregate of cells, or an aggregate of macromolecules. This differs from simpler SELEX targets which are typically isolated soluble molecules, such as proteins. In the preferred embodiment, tissues are insoluble macromolecules which are orders of magnitude larger than simpler SELEX targets. Tissues are complex targets made up of numerous macromolecules, each macromolecule having numerous epitopes can be proteins, lipids, carbohydrates, etc., or combinations thereof. Tissues are generally a physical array of macromolecules that can be either fluid or rigid, both in terms of structure and composition. Extracellular matrix is an example of a more rigid tissue, both structurally and compositionally, while a membrane bilayer is more fluid in structure and composition. Tissues are generally not soluble and remain in solid phase, and thus partitioning can be accomplished relatively easily. Tissue includes, but is not limited to, an aggregate of cells usually of a particular kind together with their intercellular substance that form one of the structural materials commonly used to denote the general cellular fabric of a given organ, e.g., kidney tissue, brain tissue. The four general classes of tissues are epithelial tissue, connective tissue, nerve tissue, and muscle tissue.

Examples of tissues which fall within this definition include, but are not limited to, heterogeneous aggregates of macromolecules such as fibrin clots which are acellular; homgeneous or heterogeneous aggregates of cells; higher ordered structures containing cells which have a specific function, such as organs, tumors, lymph nodes, arteries, etc.; and individual cells. Tissues or cells can be in their natural environment, isolated, or in tissue culture. The tissue can be intact or modified. The modification can include numerous changes such as transformation, transfection, activation, and substructure isolation, e.g., cell membranes, cell nuclei, cell organelles, etc.

Sources of the tissue, cell or subcellular structures can be obtained from prokaryotes as well as eukaryotes. This includes human, animal, plant, bacterial, fungal and viral structures.

"Nucleic acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the individual nucleic acid bases or to the nucleic acid as a whole. Such modifications include, but are not limited to, modified bases such as 2'-position sugar modifications, 5-position pyrimidine modifications, 8-position purine modifications, modifications at cytosine exocyclic amines, substitution of 5-bromo=uracil; backbone modifications, methylations, unusual base-pairing combinations such as the isobases isocytidine and isoguanidine and the like. Modifications can also include 3' and 5' modifications such as capping. Modifications that occur after each round of amplification are also compatible with this invention. Post-amplification modifications can be reversibly or irreversibly added after each round of amplification. Virtually any modification of the nucleic acid is contemplated by this invention.

"Nucleic acid test mixture" or "nucleic acid candidate mixture" is a mixture of nucleic acids of differing, randomized sequence. The source of a "nucleic acid test mixture" can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process. The length of the randomized section of the nucleic acid is generally between 8 and 250 nucleotides, preferably between 8 and 60 nucleotides.

"Nucleic acid ligand" is a nucleic acid which has been isolated from the nucleic acid candidate mixture that acts on a target in a desirable manner. Examples of actions on a target in a desirable manner include, but are not limited to binding of the target, catalytically changing the target, reacting with the target in a way which modifies/alters the target or the functional activity of the target, covalently attaching to the target as in a suicide inhibitor, facilitating the reaction between the target and another molecule. In most, but not all, instances this desirable manner is binding to the target. In the most preferred embodiment, a nucleic acid ligand is a non-naturally occurring nucleic acid ligand having a specific binding affinity for a tissue target molecule, such target molecule being a three dimensional chemical structure other than a polynucleotide that binds to said nucleic acid ligand through a mechanism which predominantly depends on Watson/Crick base pairing or triple helix binding, wherein said nucleic acid ligand is not a nucleic acid having the known physiological function of being bound by the target molecule. Nucleic acid ligand includes nucleic acid sequences that are substantially homologous to the nucleic acid ligands actually isolated by the Tissue SELEX procedures. By substantially homologous it is meant a degree of primary sequence homology in excess of 70%, most preferably in excess of 80%. In the past is has been shown that the sequence homologies of various nucleic acid ligands to a specific target shows that sequences with little or no primary homology may have substantially the same ability to bind the target. For these reasons, this invention also includes nucleic acid ligands that have substantially the same ability to bind a target as the nucleic acid ligands identified by the Tissue SELEX process. Substantially the same ability to bind a target means that the affinity is within a few orders of magnitude of the affinity of the ligands described herein. It is well within the skill of those of ordinary skill in the art to determine whether a given sequence—substantially homologous to those specifically described herein—has substantially the same ability to bind a tissue target.

"Partitioning" means any process for separating nucleic acid ligands from the remainder of the unreacted nucleic acid candidate mixture. Partitioning can be accomplished by various methods known in the art. Filter binding, affinity chromatography, liquid-liquid partitioning, filtration, gel shift density gradient centrifugation are all examples of suitable partitioning methods. Equilibrium partitioning methods can also be used as described in detail below. Since the tissue targets of the present invention are non-soluble, there are numerous simple partitioning methods which are well suited to this invention. The simple partitioning methods include any method for separating a solid from a liquid, such as, centrifugation with and without oils, membrane separations and simply washing the insoluble tissue target. The ligands can also be specifically eluted from the target with a specific antibody or ligand. The choice of partitioning method will depend on properties of the target and the nucleic acid and can be made according to principles and properties known to those of ordinary skill in the art.

"Amplifying" means any process or combination of process steps that increases the amount or number of copies of a molecule or class of molecules. In preferred embodiments, amplification occurs after members of the test mixture have been partitioned, and it is the facilitating nucleic acid associated with a desirable product that is amplified. For example, amplifying RNA molecules can be carried out by a sequence of three reactions: making cDNA copies of selected RNAs, using the polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method should result in the proportions of the amplified mixture being essentially representative of the proportions of different sequences in the mixture prior to amplification. It is known that many modifications to nucleic acids are compatible with enzymatic amplification. Modifications that are not compatible with amplification can be made after each round of amplification, if necessary.

"Randomized" is a term used to describe a segment of a nucleic acid having, in principle, any possible sequence over a given length. Randomized sequences will be of various lengths, as desired, ranging from about eight to more than one hundred nucleotides. The chemical or enzymatic reactions by which random sequence segments are made may not yield mathematically random sequences due to unknown biases or nucleotide preferences that may exist. The term "randomized" is used instead of "random" to reflect the possibility of such deviations from non-ideality. In the techniques presently known, for example sequential chemical synthesis, large deviations are not known to occur. For short segments of 20 nucleotides or less, any minor bias that might exist would have negligible consequences. The longer the sequences of a single synthesis, the greater then effect of any bias.

A bias may be deliberately introduced into a randomized sequence, for example, by altering the molar ratios of precursor nucleoside (or deoxynucleoside) triphosphates in the synthesis reaction or the ratio of phosphoramidites in the chemical synthesis. A deliberate bias may be desired, for example, to affect secondary structure, to introduce bias toward molecules known to have facilitating activity, to introduce certain structural characteristics, or based on preliminary results.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate an enriched candidate mixture. The SELEX Patent Applications also describe ligands obtained to a number of target species, including both protein targets where the protein is and is not a nucleic acid binding protein.

SELEX provides high affinity ligands of a target molecule. This represents a singular achievement that is unprecedented in the field of nucleic acids research. The present invention applies the SELEX procedure to more complicated tissue targets.

Negative selection (Counter-SELEX) is optionally employed before, during or after the Tissue SELEX process. The negative selection provides the ability to discriminate between closely related but different tissue types. For example, negative selection can be introduced to identify nucleic acid ligands that have a high specificity for a tumor cell but do not recognize the cognate normal tissue. Similarly, nucleic acid ligands can be identified which specifically recognize atherosclerotic arterial tissue but not normal arterial tissue. Nucleic acid ligands which recognize fibrin, but not fibrinogen can also be identified by this method. Additionally, nucleic acid ligands to a cell type which express a certain receptor can be counter-selected with a cell line engineered not to express the receptor (or other such macromolecule).

One of ordinary skill in the art will readily understand that various mechanisms can be employed to accomplish this negative selection. The following examples are provided mostly for illustrative purposes and are not meant in any way as limiting the procedures of negative selection. Negative selection or Counter-SELEX methods were first described in U.S. patent application Ser. No. 08/134,028, filed Oct. 7, 1993, entitled "High-Affinity Nucleic Acid Ligands that Discriminate Between Theophylline and Caffeine", which is herein incorporated by reference. A particular implementation of negative selection is embodied using equilibrium partitioning. In this method, two cell lines or other tissue types are separated by a semi-permeable membrane (0.45–0.90 μm pore size) in an equilibrium dialysis chamber; one cell line is the neoplastic target cell line, the other, the normal tissue used for the negative selection. The choice of cell or tissue type for the negative selection will be determined by the specific end results desired and will sometimes consist of a non-malignant cell line of the same tissue type as the neoplastic target. For other experiments, various normal cell types could be combined to create the negative epitope ∓sink."The random pool of nucleic acids is placed into the dialysis chamber (on the side of the normal cells; this avoids background from high avidity targets which are common to both the tumor and normal cells) and allowed to equilibrate between the two cell lines. Those nucleic acid sequences that remain bound to the target cell line or tissue at equilibrium are selectively recovered and amplified for the next round of SELEX.

This example of negative selection methodology is quite powerful. First, equilibrium dialysis negative selection allows the positive and negative selection to be carried out simultaneously. Second, the stringency of the negative selection can be varied through the alteration of the relative amounts of "positive" and "negative" cells placed on each side of the dialysis membrane. These two characteristics of equilibrium dialysis negative selection allow precise control over the evolution of nucleic acid ligands specific for the target cell or tissue type.

This same type of equilibrium partitioning negative selection can be carried out with adherent cell lines. In this embodiment, monolayers of target and negative cells or tissues are plated in different wells of a multi-welled plate. After adherence, media, along with an oligonucleotide pool, is added such that the wells are connected by the volume of cell media. After equilibration of the oligonucleotide pool, those sequences bound by the target cell line or tissue type would be isolated and amplified for the next round of SELEX.

The equilibrium negative selection strategies above offer a powerful way of generating nucleic acid ligands to tissue targets and especially tumor associated antigens (TAAs).

Additionally, there are several other negative selection methods, which could be classified as "post-SELEX screening procedures." The most simple of these procedures is the testing of individual nucleic acid ligands (those sequences generated by tissue SELEX and demonstrated to be high-affinity ligands for the tissue target) against normal tissue for cross-reactivity. However, this approach is a tedious and time-consuming process.

A more fruitful "post-SELEX" method is to perform a negative selection, for example using a normal tissue as the negative selection target, on a pool that has already been evolved from a SELEX against a desirable complex tissue target, for example a transformed cell line. This example would suggest the performance of two to three negative selections on a normal tissue using a late-round, highly evolved pool from a SELEX of a transformed cell line. The binding of certain sequences to the normal tissue would be used to subtract these sequences from the evolved pool. This method allows one to quickly eliminate from several hundred to several thousand nucleic acid sequences that show a high affinity for those targets common to both the normal and the transformed cell lines.

Another "post-SELEX" screening method is a variation of the photocrosslinking experiment described in Example two below. As an example, it is possible to synthetically incorporate a highly photoreactive nitrine group (which is also iodinatable) on the 4' end of a PCR primer used in the tissue SELEX protocols. Late-round pools from for example, a tumor cell line SELEX would be amplified with this photoactivatable (and $^{125}$I-labeled) primer, and this sequence pool would then be irradiated in the presence of the tumor cell line, and in the presence of normal tissue. Membrane proteins would be isolated and solubilized for analysis on an SDS gel. One would expect to see many different protein epitopes tagged by specific oligonucleotide sequences, for both the tumor and the normal cell lines. A few tagged targets will be unique to the tumor cell line. Because the oligonucleotides have been photochemically linked to the protein targets in a manner which does not destroy the base sequence of the oligonucleotide, it is possible to isolate a tumor-specific band from an SDS gel, and use PCR to recover a specific sequence motif that recognizes a particular tumor antigen. Thus, in one step, it will be possible to remove from a pool oligonucleotide sequences that recognize possibly hundreds of cell surface antigens, leaving one or a few families of sequences that bind specifically to a single tumor-specific antigen.

As described above, the Tissue SELEX methods can include the identification of macromolecules which comprise new epitopes on the tissue target. The nucleic acid ligand to the new epitope component of the macromolecule can be employed to purify, identify and characterize the macromolecule. The new macromolecule can be a previously unknown protein or peptide, lipid, carbohydrate, etc. Virtually any molecule that is part of the molecular make-up of a tissue can be identified by the Tissue SELEX process.

In order to fully exploit this aspect of the invention, it is important to develop strategies for the purification and identification of new macromolecules which comprise the new epitopes and to determine the roles these new macromolecular components of the tissue play in biological systems. The methods for purifying new macromolecules are well-known, especially in the art of protein purification. These standard purification methods include crosslinking, affinity chromatography, peptide microsequencing, Edman sequencing, mass spectrometry, and cDNA library searches.

The following discussion describes this process as it would be applied to the identification of a new tumor-associated antigen (TAA). For the purposes of this discussion, a TAA is a macromolecule that is expressed on a tumor cell, but not on a similar normal cell. A TAA may or may not be immunogenic. A TAA is merely one example of the kinds of macromolecules which can be identified by the Tissue SELEX process and simply used for illustrative purposes. However, it is readily apparent that this process can be extrapolated to any new macromolecule identified by the Tissue SELEX process.

As applied to TAAs, the identification of new TAAs by the Tissue SELEX process is composed of two main parts: one, developing strategies for the purification and identification of new TAAs, and two, the elucidation of the role these tumor antigens play in cancer (i.e., determining the biological significance of each particular TAA in the development and progression of a particular cancer).

The steps of purification and identification of most of the TAAs should be straightforward and understood by one skilled in the art of protein purification. As with antibodies, SELEX provides a reagent—a high-affinity ligand specific for the tumor antigen—that is incredibly useful for the purification of the antigen from whole cells or other tissues. As a non-limiting example, most antigens will be amenable to some type of photo-affinity crosslinking as described in the RBC ghost SELEX experiments of Example 1 or in the negative selection strategies section above. Specific crosslinking of the TAA, using a photoactivatable oligonucleotide with a 3' biotin conjugate will allow one-pass purification of the TAA target using strepavidin coated beads. An alternative method to this purification strategy is to use a column-bound high-affinity nucleic acid ligand to affinity purify the TAA target from solubilized target cell membrane preparations.

There are many compelling reasons to believe that the method provided herein for identifying macromolecules that comprise new epitopes on tissues offers distinct advantages over traditional methods of new macromolecule discovery. Again, the following discussion will be directed to tumor-associated antigen discovery, but one will readily understand that it can be broadly extrapolated to all new macromolecule discovery.

As applied to tumor-associated antigens, one must fully consider that all that is known about tumor antigens has been derived from the immune system's reaction to particular antigens; science has depended on the particular restrictions of the immune system, and the system's repetoires to distinguish antigenic differences between neoplastic and normal tissue. It is entirely possible that other tumor antigens exist that are not subject to immune response. Some investigators have hypotesized that there may in fact be many antigenic differences between cancer and normal tissue, which are, unfortunately, not immunogenic.

The SELEX methodology provides an improved way to identify TAAs that avoids the restrictions posed by the immune system:

a. SELEX can actually provide a deeper search of TAAs than can the entire potential antibody repertoire of an organism—the size of the nucleic acid libraries used in SELEX is unrivaled by any biological system;

b. SELEX provides nucleic acid ligands to targets, including those which are not antigenic to the immune system because of tolerance. Many of the TAAs which have been identified are oncofetal—they are antigens expressed at some point during development or cell differentiation. As prior "self" antigens, they elicit no overt immune response because of earlier immune system tolerization. A SELEX-based search for TAAs avoids the circular nature of using the immune system as a means of identifying tumor antigens;

c. SELEX nucleic acid ligands have been shown to be exquisitely sensitive to target conformation. While most antibodies recognize conformational, or discontinuous eptitopes, antibody functional epitopes are composed of only a few amino acids. The potential binding surface of an oligonucleotide ligand is much larger than that of an antibody variable region, and may provide greater conformational discrimination of large targets. Additionally, cross-reactivity for SELEX ligands is substantially less of a problem than for monoclonal antibodies. A considerable set of restrictions also controls T-cell mediated tumor responses. These immune system limitations provide important biological functions; however, they limit the immune system's power for TAA identification.

d. SELEX is possibly more sensitive to small quantities of antigen than the immune system. Although the immune sysetm's threshold for reactivity has been estimated to be 200 copies/cell for an antigenic MHC-presented peptide, a B-cell antibody response (necessary for any antigen that is not a peptide—cabohydrates, lipids or conformational antigens) to a monovalent target requires antigen concentrations of about 100 mM. SELEX can generate ligands to TAA targets with a low representation on the cell surface;

e. SELEX provides a rapid and thorough method of TAA discovery. Screening of monoclonal antibodies to tissue sections, and purification and identification of MHC peptides are painstaking processes that set practical limits on the depth and completeness of searches for TAAs. Tissue SELEX experiments take a much abbreviated length of time.

Nucleic acid ligands to tissue targets or the tissue epitopes identified by the method of the invention are useful as diagnostic reagents and as pharmaceuticals. The nucleic acid ligands are also useful for the identification of new macromolecules. The nucleic acid ligands are useful in any application that would be suitable for use of an antibody.

As diagnostic reagents, the ligands or tissue epitopes can be used in both in vitro diagnostics and in vivo imaging applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek for a diagnostic ligand. Details regarding use of the ligands in diagnostic applications is well known to one of ordinary skill in the art. Nucleic acid ligands that bind specifically to pathological tissues such as tumors may have a role in imaging pathological conditions such as human tumor imaging and even therapeutic delivery of cytotoxic compounds or immune enhancing substances.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labelling tag in order to track the presence of a ligand. Such a tag could be used in a number of diagnostic procedures.

Specifically, oligonucleotide ligands with high specificity for particular tumor antigens could become as important as monoclonal antibodies for the detection, imaging, and surveillance of cancer. Modified nucleic acid ligands show nuclease resistance in plasma, and the use of 5' and 3' capping structures will provide stability in animals that rivals that of monoclonal antibodies (and without the immunogenicity of animal-derived MAbs). Radionuclides, magnetic compounds, and the like can be conjugated to tumor-specific oligonucleotides for cancer imaging. SELEX tumor ligands can also be used to determine if these tumor antigens are sloughed off tumors, and are detectable in the plasma like PSA.

The nucleic acid ligands to tissue targets or newly identified macromolecules components of tissue are also useful as pharmaceuticals. Therapeutic uses include the treatment or prevention of disease or medical conditions in human patients. Therapeutic uses also include veterinary applications. The ligands can bind to receptors and be useful as receptor antagonists. Conversely, under certain circumstances the ligands can bind to receptors and cause receptor capping and act as receptor agonists.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

Standard formulations can e used for the nucleic acid ligands of the invention and are known to one of ordinary skill in the art.

The following examples provide a non-limiting description of the present invention. Example One describes obtaining ssDNA ligands to the complex tissue target red blood cell ghosts. The red blood cell ghost comprises a finite set of membrane-bound epitopes and is a non-living target which remained unchanged over the period of the selection. Ligands to RBC ghosts have numerous uses including, but not limited to, the ability to in vivo image extravascular blood as is desirable for head or retroperitoneal injuries or to extend the vascular half-life of other ligands that may be attached to the RBC ghost ligand. Example Two describes the identification of a macromolecule component on the RBC ghost using a ligand obtained in Example One. Example Three demonstrates that red blood cell ghost SELEX has produced high affinity and high specificity ligands to more than one macromolecular component of the target cell membrane. Example Four describes the identification of and enrichment for high affinity nucleic acid ligands which bind individual components of a complex macromolecular target. Example Five describes obtaining ssDNA ligands to a glioblastoma cell line. High affinity and specificity nucleic acid ligands were isolated that may interact with tumor-associated (or tumor-specific) antigens, or mimic cytokines in their interactions with cell surface receptors causing cell morphology changes. Ligands to glioblastoma cell lines have numerous uses including, but limited to, in vivo imaging of glioblastomas, therapeutic localization of the ligand or other therapeutic agents that are attached thereto. Example Six describes ssDNA ligands to a human lymphoma cell line.

EXAMPLE ONE ssDNA Ligands to Red Blood Cell Ghosts

This example demonstrates the ability to obtain ssDNA ligands to the complex tissue target human red blood cell ghosts (RBC ghosts). Red blood cell preferentially resealed in a right-side-out manner (Steck et al. (1994) Biochemistry 10:2617–2624). Red blood cell ghosts were the first complex tissue target on which in vitro selection was performed. The red blood cell ghost is one of the least complicated tissue targets and yet is still orders of magnitude more complex than the pure proteins or small molecules previously used for SELEX procedures. The red blood cell ghost comprises a finite set of membrane-bound epitopes and is a non-living target which remained unchange over the period of the selection. Ligands to RBC ghosts have numerous uses including, but not limited to, the ability to in vivo image extravascular blood as is desirable for head or retroperitoneal injuries or to extend the vascular half-life of other ligands that may be attached to the RBC ghost ligand.

Briefly, the RBC ghost SELEX was carried out with single-stranded DNA for selection, using a 30-base randomized region. The single-stranded DNA pool was incubated with RBC ghosts, and the tighter-binding sequences were partitioned from the rest of the pool by filtering the reaction through nitrocellulose filters. 25 rounds of selection were carried out, using a decreasing concentration of ghosts as the SELEX experiment progressed. The 25th round pool was cloned and sequence according to standard procedures. Listed in Table 1 are the 66 sequences isolated from the 25th round pool (SEQ ID NOS: 5–70). Approximately 60% of these sequences can be classified into seven sequence-specific motifs, there is one class of pyrimidine-rich sequences (12%), and the other 19% are "orphans," showing no similarity to other sequences.

Binding behavior of round 0 and round 25 pools, and selected clones shows that the round 25 pool binds significantly better than the starting pool, and several of the motif 1 clones bind better than the round 25 pool. All sequences tested for binding so far show similar binding to whole red blood cells, so it is believed that the SELEX ligands have evolved to membrane targets on the extracellular side of the RBC ghosts.

A. MATERIALS AND METHODS

Red blood cell ghosts

Red blood cell ghosts are erythroid cells which have been lysed, purged of their cellular contents and preferentially resealed in a right-side-out manner (Steck et al. (1994) Biochemistry 10:2617–2624). The concentration of protein in the preparation was measured with Coomassie brilliant blue G-250 (Bio-Rad).

Synthesis of initial pool of ssDNA 10 pmol of template with 30 random nucleotides flanked by fixed sequences complementary to the primers (SEQ ID NO: 1) was PCR amplified for 25 rounds in 10 mM Tris-HCl, pH 8.6, 50 mM KCl, 2.5 mM $MgCl_2$, 170 mg/ml BSA, 1 mM dNTPs, 0.5 units/ml Taq DNA polymerase and 5 mM each primer (5'-GGAGCTCAGAATAAACGCTCAA-3' (SEQ ID NO: 2) and 5'-BBBGATCCGGGCCTCATGTCGAA-3'(SEQ ID NO: 3), where B=biotin). A similar reaction contained 1 pmol of template, 0.1 mM dCTP and 1.25 mM [α-$^{32}$P]dCTP (800 Ci/mmol) to produce internally labeled ssDNA for monitoring the binding affinity of the pool. Non-biotinylated, ssDNA was purified from the larger biotinylated strand by electrophoresis in 8% polyacrylamide gels containing urea.

The SELEX Protocol 40 pmol unlabeled ssDNA and a trace amount of radioactively labeled ssDNA were denatured by heating at 70° C. for 5 min in 200 μl PBS (pH 7.3) and renatured at 0° C. for 10 min. Pre-filtration of the DNA solution was used to counter-select sequences that might bind to nitrocellulose. After washing the filter with 300 μl PBS, the ssDNA molecules passed through the filter were divided into 50 μl aliquots. An equal volume of PBS containing various concentrations of RBC ghosts (0–1.72 mg/ml total protein) was added to each aliquot. The mixture was incubated for 20 min at room temperature then filtered through nitrocellulose. The filters were washed with 5 ml PBS and the amount of radioactively labeled ssDNA retained was measured by scintillation counting. The ssDNA was isolated from the filter that retained 5–10 times the radioactivity bound to the background control filter and was amplified by PCR for the next round of selection.

Nitrocellulose filter binding assays

The nitrocellulose filter partitioning method was used as described in SELEX Patent Applications to determine the affinity of nucleic acid ligands for RBC ghosts and for other proteins. Filter discs (nitrocellulose/cellulose acetate mixed matrix, 0.45 μm pore size, Millipore) were placed on a vacuum manifold and washed with 5 ml of TBSC buffer under vacuum. Reaction mixtures, containing $^{32}$P labeled nucleic acid pools and RBC ghosts were incubated in TBSC for 5 min at 37° C., filtered, and then immediately washed with 5 ml TBSC. The filters were air-dried and counted in a Beckman liquid scintillation counter without fluor. Dissociation constants for single RBC ghost ligands were determined by Scatchard analysis (Scatchard, G. (1949) Ann. N.Y. Acad. Sci. 51:660–627; Robb, R. J., Munck, A., and Smith, K. A. (1985) J. Immunol. Methods 81:15–30), using constant ghost concentrations and varying the concentration of nucleic acid ligand. Scatchard analysis was performed using nitrocellulose partitioning of bound ligand from unbound ligand. For comparisons between random and evolved nucleic acid ligand pools, and for ligand/ligand comparisons, standard filter binding assays were used as described in the SELEX patent applications.

Cloning and nucleotide sequence determination

Individual DNA molecules were isolated from the round 25 pool by PCR amplification with primers that introduce BamHI and HindIII restriction sites at the 5' and 3' ends of the DNA. Restriction digested PCR products were ligated into pUC18 and introduced into *E. coli* strain SURE (Stratagene) by electroporation. Plasmids were isolated and the nucleotide sequences in the inserted DNAs were determined by standard dideoxynucleotide methods. The sequences were searched for patterns in their primary sequences and in their possible secondary sequences both by inspection and with the aid of computer algorithms.

B. RESULTS OF THE SELEX PROCEDURE

Clones

As described in Section A, ssDNA with 30 randomized positions was used in SELEX with RBC ghosts as the target. The affinity of the ssDNA population for the membranes increased over twenty-five rounds of selection and amplification. The round 25 PCR products were cloned and the nucleotide sequences of 66 individuals were determined as shown in Table 1 (SEQ ID NO: 5–70). Eight clones contained one 8 and one 11 nucleotide consensus sequence separated by 3 to 14 bases (SEQ ID NOs: 5–12). This group of sequences has been termed motif I sequences. Several of these clones are likely to have arisen from a single progenetor sequence by PCR mutagenesis (ie. 20, 121 and 117). One of the clones (clone 25) (SEQ ID NO:12) in this group may use a portion of the 5'-end fixed region to complete the consensus sequence. A region of this fixed sequence and the consensus sequence differ by only two nucleotides. Binding analysis of portions of the motif I sequences have defined the minimum binding sequence as the region containing no more than the 8-base and 11-base consensus sequences. Two synthetic truncate sequences have been made from the motif I sequences c56t (SEQ ID NO:4) (from parent 56) and c20t (SEQ ID NO: 236) (from parent 20). The extremely high similarity between all the motif I sequences has prevented a phylogenetic analysis of the sequences and data on the secondary structure of this motif has not been obtained as shown in FIG. 3.

Another group of 7 sequences (SEQ ID NOS: 22–25 and 35–37) contain an 18-base conserved primary sequence and share additional secondary structural elements. Computer folding algorithms and phylogenetic analysis predict a hairpin-bulge-stem structure for these sequences as shown in FIG. 3. These sequences have been termed the motif II sequences. Two synthetic truncated ligands have been made for this sequence motif, c16t (SEQ ID NO:237) (parent 16) and c79t (SEQ ID NO:238) (parent 79).

An additional group of 10 sequences share a common region of 13 bases, surrounded by additional conserved secondary structural elements. Computer folding algorithms and phylogenetic analysis predict a stem-bulge-stem structure for this group of sequences, called the motif III sequences (SEQ ID NOS: 18–21; 28–30; 40–42) as shown in FIG. 3. The similarity between the members of the motif III sequences becomes even more substantial at the secondary structure level, for the motif III ligands accomplish this structure in two different circularly permuted ways. FIG. 3 illustrates this permutation for two motif III truncate ligands, c53t (SEQ ID NO: 240) (parent 53) and c111t (SEQ ID NO:239) (parent 111).

Three more sequence motifs have been defined by sequence homology. Motif IV contains 5 members, motif V has 5 members, and motif VI 2 members as shown in Table 1. The possible secondary structures for these sets of ligands has not yet been determined.

Twenty of the sequences show no large sequence homology to other sequences and are termed orphans. While several identical clones lie within this group, these clones most likely arose from a single progenitor sequence and do not represent another "motif."

The final group of sequences showed extremely high pyrimidine content (77–90%), and no common secondary structure has been proposed.

Affinities

The binding behavior of round 0 and round 25 pools, and a selected number of round 25 clones have been tested. The round 25 pool binds approximately 10-fold better than the starting pool, and several of the motif I clones bind 100-fold better than the round 0 pool. All sequences tested for binding show similar binding to whole red blood cells, and therefore the inventors hereof believe that ligands have been selected to membrane targets on the extracellular side of the RBC ghosts.

A synthetic twenty-two nucleotide truncate of clone 56 (c56t) (SEQ ID NO: 4) that contains only the consensus sequences with four intervening nucleotides retained most of the binding affinity exhibited by the entire ssDNA sequence. A Scatchard plot analysis of c56t measured 1600 binding sites per cell, and a calculated dissociation constant of 4 nM for the target presented on the RBC ghosts. Truncate ligands from motifs II and III have not yet been analyzed for binding to the ghosts, but the photoaffinity studies of these ligands shown in Examples 3 and 4 indicates that their dissociation constants are as good or better than c56t. The pyrimidine-rich clones had affinities that were higher than the round 25 pool but lower than the consensus clones.

EXAMPLE TWO

Identification of Macromolecule Component on RBC Ghost

In order to confirm that the c56t ligand (SEQ ID NO: 4) recognizes a single, distinct target on RBC ghosts, a series of short-wavelength UV crosslinking experiments were done in an effort to photochemically link the c56t ligand to its membrane target through thyidine crosslinking. As controls, two 22-base DNA oligonucleotides of the same base composition, but scrambled in sequence were also crosslinked to the RBC ghost target. Briefly, the target recognized by c56t was identified by short wavelength (254 nm) UV crosslinking experiments. 5' $^{32}$P end labelled truncate ligand c56t, and two control oligonucleotides of the same length and base composition (but with the primary sequences scrambled using a "shuffling" computer algorithm), were irradiated in the presence of RBC ghosts. The ghost membrane proteins were fractionated using denaturing SDS gel electrophoresis, and the presence of crosslinked ligand detected by autoradiography of the dried gel. The results are shown in FIG. 1. Autoradiography indicated a single specific crosslinked product for c56t (all three oligos show slight crosslinking to two other RBC ghost proteins). The c56t ligand, but not the two controls, selectively labels an RBC ghost membrane protein with an apparent molecular weight of 105 kDa. Silver staining of this protein target indicates that it is not an abundant protein.

A similar short wavelength photoaffinity crosslinking experiment was performed using both specific and non-specific nucleic acid competitor in the photocrosslinking reaction (FIG. 3). The addition of a $10^3$ molar excess cold c56t in the reaction abolished crosslinking to the 105 kDa ghost component. However, the addition of a $10^3$ molar excess of cold motif II sequence c16t did not affect the crosslinking of c56t. This "cross competition" experiment demonstrates the incredible affinity and specificity of the truncate ligand c56t with its protein target.

Figure 2:
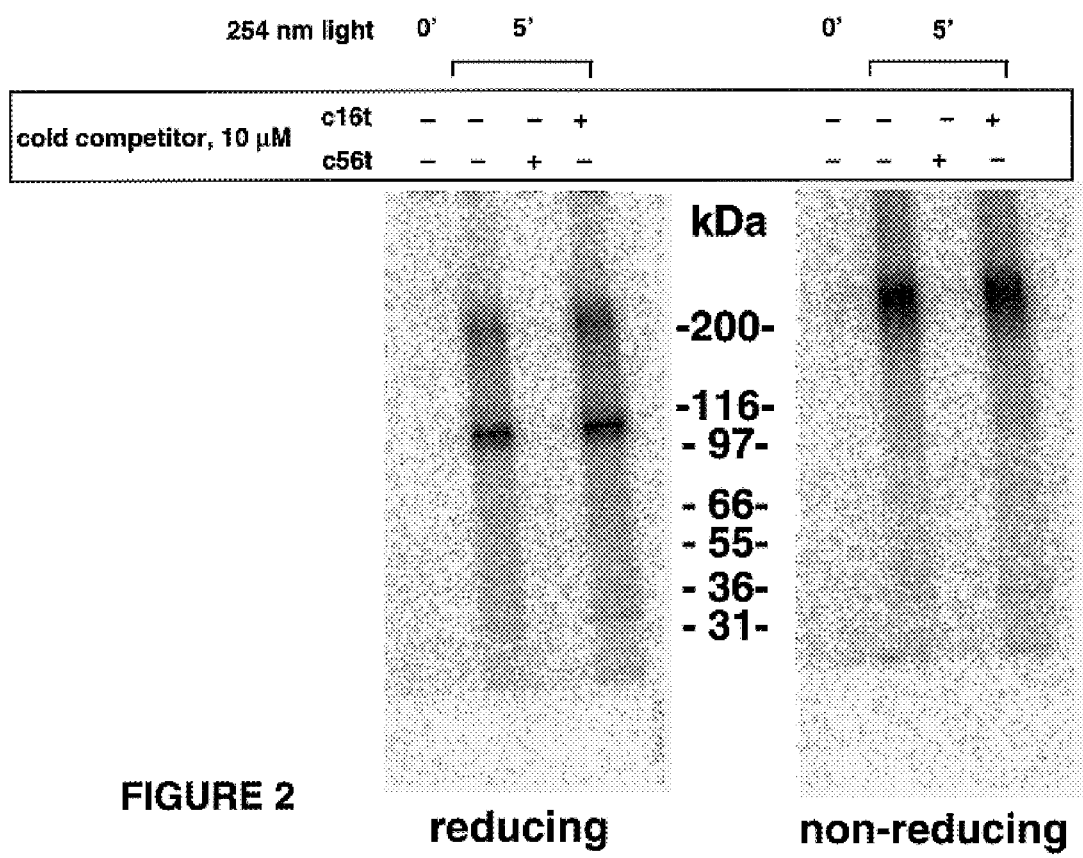
FIG. 2 shows the photoaffinity crosslinking of the truncate ligand c56t to RBC ghosts. $10^7$ ghosts were mixed with 1 nM of c56t and irradiated with a 254 nm hand-held transilluminator for 0 or 5 minutes. The irradiations were performed in the absence of cold competitor, with 10 $\mu$M cold c56t (as a specific competitor) or 10 $\mu$M cold c16t (as a non-specific competitor). The photoaffinity reactions demonstrate the high affinity and high specificity of the ligand-protein interaction. Shown are SDS-PAGE results under both reducing and non-reducing conditions (both conditions are denaturing). The doubling of the molecular weight of the crosslinked protein under non-reducing conditions suggests the target protein is a disulfide-linked hetero- or homo-dimer.

Additionally, the product of the photoaffinity crosslinking reaction was examined under both reducing and non-reducing SDS-PAGE as shown in FIG. 2. Under reducing conditions, the crosslinked protein runs with an apparent molecular weight of 105 kDa. Under non-reducing conditions, the crosslinked protein migrates at about 210 kDa, and suggests that the crosslinked protein is present on the ghost membrane as a disulfide-linked hetero- or homo-dimer. At present, only two human CD antigens that are disulfide bonded homodimers with monomer molecular weights within the range of 90–110 kDa are known, and only one is present on red blood cells and its direct progenitors. This antigen is the transferrin receptor (with a monomer molecular weight of 95 kDa). A definitive demonstration of the identity of the protein crosslinked by c56t is under investigation.

EXAMPLE THREE

Red Blood Cell Ghost SELEX has produced high affinity and high specificity ligands to more than one macromolecular component of the target cell membrane A key assumption of tissue SELEX is that nucleic acid selection of collections of large macromolecular structures should result in the generation of high affinity ligands to all independent binding sites on these structures. Since cells or tissues are many magnitudes of order larger than a purified protein target, the number of these independent binding sites should be large. In brief, this theory predicts that selection of multiple targets produces ligands with multiple binding specificities.

Figure 4:
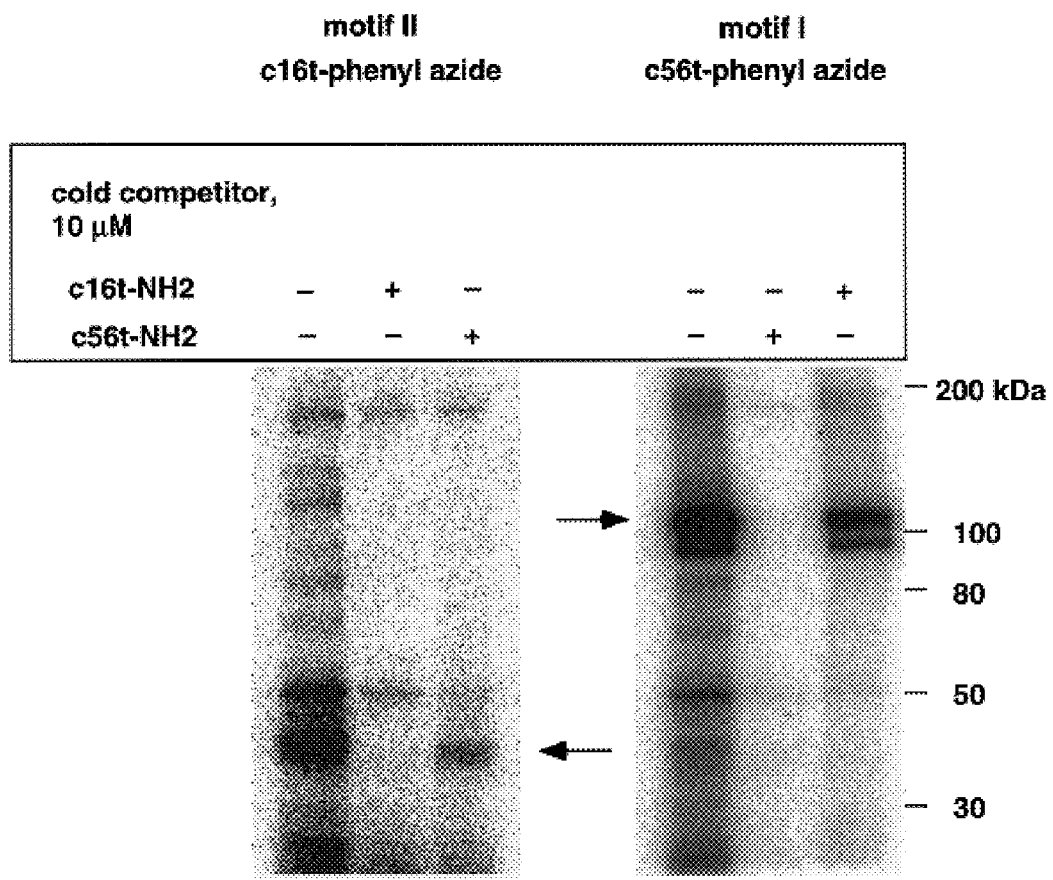
FIG. 4 displays affinity photocrosslinking data for the motif I truncate c56t and the motif II truncate c16t. The nucleic acid ligands have been synthesized as shown in FIG. 1 with a six-carbon amino linker on the 5' end of each molecule. These 5' modified ligands were radiolabeled on their 3' end with alpha $^{32}$P ddATP. The amino linker was used to conjugate the ligands with the photocrosslinking reagent sulfo-HSAB. Approximately 5 nM ssDNA was mixed with 10 mM sulfo-HSAB in 200 mM triethylamine $CO_2$ (pH 9.5) and allowed to react 15 min. at room temperature and 15 min. at 37 degrees C. Approximately $10^7$ ghosts were mixed with 10 nM of each ligand conjugate in a volume of 15 μl, incubated 30 min. at room temperature and irradiated for 100 pulses of a 308 nm excimer laser (175 mJ/pulse/cm$^2$). The reaction was then mixed with an equal volume of 2X reducing SDS loading buffer and run on a 4–12% gradient SDS polyacrylamide gel. The gel was run, fixed and dried. Radioactivity was detected by a Fuji phosphorimager. Shown are photocrosslinking reactions as described above for c56t and c16t, with two additional reactions for each ligand: one included the addition of 10 μM cold, unconjugated c56t, the other the same concentration of c16t. These "cross competition" reactions demonstrate the high affinity and specificity of the photoaffinity crosslinking method.

Thus the selection of red blood cell ghosts should result in the evolution of high affinity nucleic acid ligands to more than one, and potentially all protein targets present on the membrane surface. In an effort to provide definitive proof of this hypothesis, truncate ligands from the first two red blood cell ghost sequence classes (motif I and II; see FIG. 3) were affinity photocrosslinked to the ghost membranes. Truncates c56t (motif I) (SEQ ID NO: 4) and c16t (motif II) (SEQ ID NO: 237) were made synthetically, with the addition of a primary aliphatic amine (with a six carbon spacer group) on the 5' end of each molecule. This amino group was used to conjugate the truncate ligands to the phenyl azide photoreactive molecule sulfo-HSAB (N-hydroxysulfo-succinimidyl 4-azidobenzoate, Pierce Chemical Company). Additionally, these molecules were radiolabeled on their 3' end using alpha 32' ddATP. The truncate ligand conjugates were mixed with ghosts and photocrosslinking carried out using a 308 nm excimer laser as shown in FIG. 4. To demonstrate high affinity and specificity, the photoreactive truncates were irradiated with the ghosts in the presence of cognate or non-cognate unradiolabeled, unconjugated truncate.

The motif I truncate ligand c56t specifically labels a dimer protein band of apparent molecular weight of 105 kDa, the identical protein band labeled by this truncate using short wavelength UV photocrosslinking. The photoaffinity crosslinking can be prevented by the addition of $10^4$ molar excess of "cold" c56t, but not by the addition of $10^4$ molar excess of cold c16t. Similarly, the motif II truncate specifically labels a protein of apparent molecular weight of 40 kDa. This crosslink can be prevented by the addition of cold c16t but not by cold c56t. Thus, it is clear the red blood cell ghost SELEX has produced high affinity and high specificity ligands to more than one macromolecular component of the target cell membrane.

This photoaffinity analysis has now been carried out for all truncate ligands shown in FIG. 3. The motif I truncate c20t (SEQ ID NO:236) specifically labels the same protein dimer band as the motif I truncate c56t, and the motif II truncate c79t (SEQ ID NO: 238) labels the same 40 kDa protein band at the motif II truncate c16t. The two motif III truncate ligands c53t (SEQ ID NO:240) and c111t (SEQ ID NO: 239) specifically label a group of three proteins ranging in molecular weight from 42–55 kDa, and presumably these proteins are physically associated as a protein complex on the ghost membranes. This consistent pattern of identical photoaffinity crosslinking behavior within sequence motifs, and different protein bands crosslinking among motifs is very strong proof of the fundamental hypothesis of tissue SELEX—multiple targets result in ligands with multiple specificities.

EXAMPLE FOUR

Identification of and enrichment for high affinity nucleic acid ligands which bind individual components of a complex macromolecular target After the generation by tissue SELEX of high affinity ligands to many targets within a complex mixture, it is desirable to be able to screen this large pool of sequences for those nucleic acid molecules which recognize a particular, discrete target within the complex mixture. A method for this procedure has been developed for the red blood cell ghost SELEX which has been termed "pool deconvolution." The pool of sequences from the final round of the RBC ghost SELEX (round 25) was amplified using internal radiolabel and a "sense strand" PCR primer which carried the same primary amine, six carbon spacer described in Example Three at its 5' end. Thus, every sequence in the purified ssDNA pool contained this primary amino group at their 5' end. The pool of sequences was conjugated to the phenyl azide compound sulfo-HSAB, purified, and incubated with the RBC ghosts in the presence of $10^3$ molar excess of non-specific nucleic acid competitor. The mixture was irradiated using a 308 nm excimer laser and the crosslinked products separated by SDS-PAGE.

Figure 5:
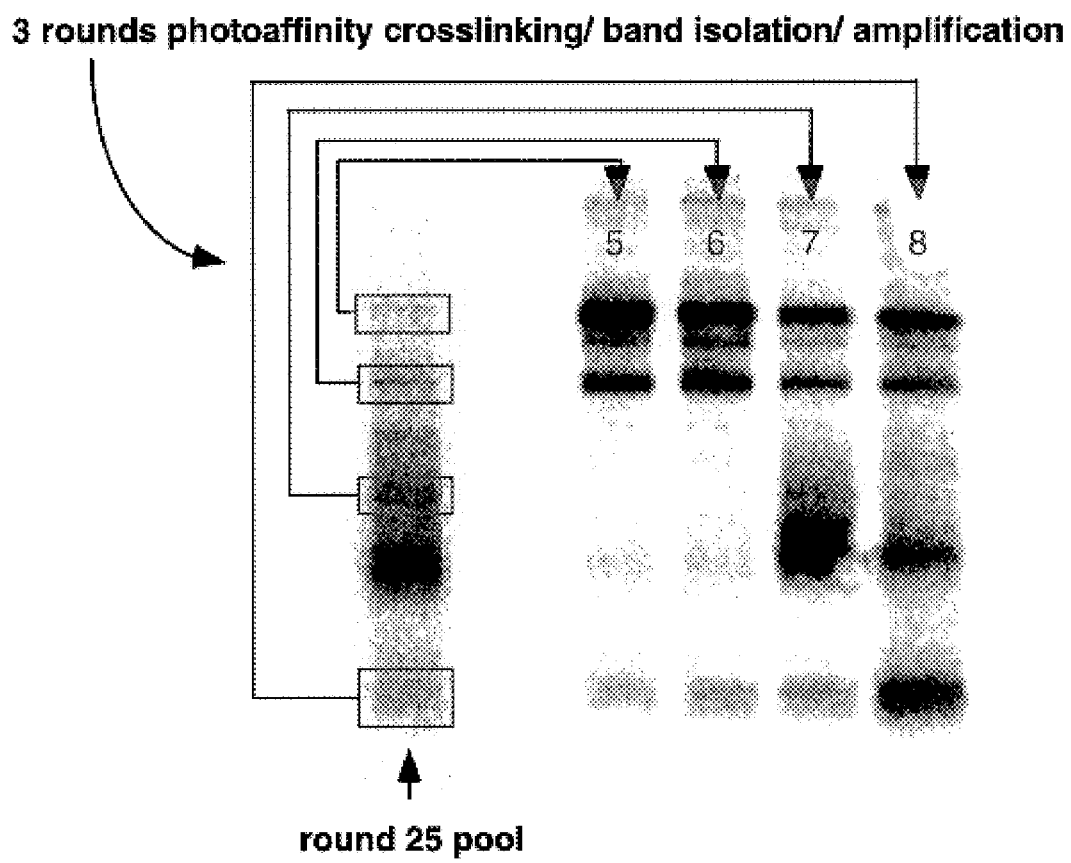
FIG. 5 shows the results of three rounds of selection for sequences within the final round rbc ghost SELEX pool that are specific for four distinct proteins on the rbc ghost membrane. The final round SELEX pool (round 25) was amplified using a "sense-strand" primer synthesized with a 5' six carbon amino linker group. The PCR product was radiolabeled with 3,000 Ci/mmol, 1.3 μM (final) alpha $^{32}$P dCTP ([cold dNTPS]=100 μM (final)). The sense strand was purified using denaturing PAGE and eluted from the gel matrix and precipitate. The phenyl azide compound sulfo-HSAB was conjugated to the pool and the nucleic acid conjugate used for photoaffinity crosslinking with the rbc ghosts. $10^7$ ghosts were irradiated with 10 nM pool conjugate in a volume of 15 μl and in the presence of 12 μM non-specific nucleic acid competitor (a 30 base random pool). The reaction was incubated for 30 min. at room temperature and irradiated for 100 pulses of a 308 nm excimer laser (175 mJ/pulse/cm$^2$). The reaction was then mixed with an equal volume of 2X reducing SDS loading buffer and run on a 4–12% gradient SDS polyacrylamide gel. The gel contents were electroblotted to a nitrocellulose filter, the filter washed in water and dried. Radioactivity was detected by a Fuji phosphorimager. DNA sequences which showed crosslinking to four proteins (termed proteins 5, 6, 7, and 8) varying in apparent molecular weight from 170–30 kDa were isolated by sectioning the nitrocellulose filter and placing the appropriate filter slices directly into PCR reactions for sequence amplification. The sequences were amplified for approximately 22 rounds, the sense strand purified, and the DNA reamplified for another 22 rounds. The resulting DNA was again purified, conjugated to sulfo-HSAB and used for the next round of photoaffinity crosslinking.

The crosslinking pattern of the final round pool is shown in FIG. 5. One can clearly see that many different proteins present in the ghost membrane have been specifically photolabeled by the pool sequences. The SDS-PAGE separated products were electroblotted to a nitrocellulose filter, and sections of the filter which corresponded to four different crosslinked proteins were excised and placed in PCR reactions for amplification of the pool sequences which crosslinked to the particular protein selected. This "deconvolution SELEX" was carried out for three rounds, and the results of the selections are shown in FIG. 5. Lanes numbered 5, 6, 7, and 8 correspond to the four selected protein bands as indicated on the round 25 lane. The three rounds of selection has produced excellent enhancement for sequences which can specifically photocrosslink to selected ghost membrane proteins. The pools used to produce lanes 5 and 8 are both close to becoming completely specific for the selected proteins. The stringency of further selections will be increased by using high concentrations of non-specific competitor nucleic acid and by competing a particular pool (such as that for band 5) with cold, non-conjugated fractions of the remaining three pools. Such a scheme should allow the selective removal of sequences that are common to two or more pools. For example, competing the photocrosslinking of the pool for band 5 with cold material from the band 6, 7, and 8 pools should eliminate the common crosslinking between the band 5 pool and the other pools. When the selection is completed, the isolated DNA for a particular protein band can be readily sequenced by standard methods, allowing one to correlate particular nucleic acid sequences with high affinity binding to a discrete protein. This deconvolution technique is a powerful method for screening high affinity tissue SELEX pools for sequences which bind a particular target of interest.

EXAMPLE FIVE ssDNA Ligands to Glioblastoma U251 Cell Line

This example demonstrates the ability to obtain ssDNA ligands to the complex tissue target glioblastoma cell line U251, which is derived from human brain tumor (Hum. Hered. (1971) 21:238). High affinity and specificity nucleic acid ligands were isolated that may interact with tumor-associated (or tumor-specific) antigens, or mimic cytokines in their interactions with cell surface receptors causing cell morphology changes. Many of the protocols used in this example are outlined in Example One or are slightly varied as described below. Ligands to glioblastoma cell lines have numerous uses including, but not limited to, in vivo imaging of glioblastomas, therapeutic localization of the ligand or other therapeutic agents that are attached thereto.

In this tissue SELEX example, a fluorescent-labeled single-stranded DNA library with 34 nucleotide randomized region was used (SEQ ID NO: 71). The fluorescent-labeled ssDNA was purified by denaturing polyacrylamide gel. The sequences of primers and template are as follows:

5'-primer; 5'-F-GCCTGTTGTGAGCCTCCT-3' (F: fluorescein) (SEQ ID NO: 72)

3'-primer: 5'-GGGAGACAAGAATAAGCG-3' (SEQ ID NO: 73)

template: 55'-GCCTGTTGTGAGCCTCCT-N34-CGCTTATTCTTGTCTCCC-3' (SEQ ID NO: 71)

Briefly, the SELEX procedure was as follows. One to 10 million glioblastoma cell line U251 cells were washed twice in a culture flask with 20 mL cold RPMI-1640 serum-free medium at 4° C. 50–100 picomoles of ssDNA in 100 μL PBS buffer was heated at 90° C. for 5 minutes and put on ice for 5 minutes. The ssDNA pool was added to the cell culture in 20 mL RPMI-1640 medium along with 20–40 fold excess sonicated sperm DNA and yeast tRNA (molar ratio 1:1). The solution was incubated at 4° C. for 20 minutes with gentle shaking. The cells were washed twice with 20 mL cold RPMI-1640 medium to remove the free oligonucleotides. The cells were tryopsinized with 1 mL of 0.25% trypsin. The solution that contains cells and oligonucleotides was collected to a 2 mL tube, boiling at 95° C. for 5 minutes, followed by phenol extraction and ethanol precipitation. The recovered ssDNA was used for PCR amplification. Through 20 rounds of selection, the binding affinity of the final pool was significantly increased comparing with that of the starting material. The affinity increase was revealed by Scatchard graph. The round-20 pool was cloned into pUC18 vector by DUG cloning as described by Rashtchain et al. (Anal. Biochem. (1992) 206:91). About 158 sequences were obtained, which can be grouped into 22 subfamilies and are shown in Table 2 (SEQ ID NOs: 74–232).

EXAMPLE SIX ssDNA Ligands to Human Lymphoma Cell Line

This example demonstrates the ability to obtain ssDNA ligands to the complex tissue target human lymphoma cell line CEMss, which is a CD4 positive cell line (Foley et al., Cancer (1965) 18:522). Many of the protocols used in this example are outlined in Example One or are slightly varied as described below.

In this tissue SELEX example, fluorescein labeled single-stranded DNA molecules were used for the generating of combinatorial library. The fluorescein-labeling allows for image of oligonucleotides binding to the cell surface and for the purpose of flow cytometry. The sequences of primers and templates are as follows:

5'-primer: 5'-F*-GCCTGTTGTGAGCCTCCT-3' (F*= fluorescein) (SEQ ID NO: 233)

3'-primer: 5'-GGGAGACAAGAATAAGCG-3' (SEQ ID NO: 234)

template: 5'-GCCTGTTGTGAGCCTCCT---$N_{34}$---CGCTTATTCTTGTCTCCC-3' (SEQ ID NO: 235)

Briefly, the SELEX procedure was as follows. The target cell line was the human lymphoma cell line CEMss, which is CD4 positive. 5×10⁶ cells were washed twice with 10 mL of cold PBS buffer in a 15 mL conical tube. The cells were resuspended with 1 mL PBS and stored on ice. 50–100 picomoles of fluorescein-labeled (and $^{32}$P-internally-labeled by PCR) single-stranded DNA (SEQ ID NO: 235) in 100 μL PBS was heat denatured at 90° C. for 5 minutes, and was kept on ice for 5 minutes. Incubate the single-stranded DNA together with 20–50 fold excess competitor yeast tRNA and sonicated denatured sperm DNA (ratio: 1 to 1), with cells at room temperature for 20 minutes with gentle shaking. Load the reaction solution on top of 0.5 mL of binding oil (84% silicon oil and 16% paraffin oil), spin at top speed for 15 seconds, immediately freeze in dry ice/ethanol. Cut the bottom tip of the tube off and put the tip in a 2 mL tube, add 100 μL water, 100 μL 7 M urea, and 400 μL phenol, shake and boil for 5 minutes. Count the cpm, then shake for another 20 minutes, spin at top speed for 10 minutes, transfer the top phase to a new tube and ethanol precipitate. The recovered DNA was PCR amplified and purified on a denaturing gel. The fluorescein-labeled strand migrates slower. The recovered ssDNA was used for next round of SELEX.

The improvement of binding affinity was determined by binding assay. The reaction condition was as described above, with the exception that the reaction volume is 100 μL, without the addition of competitor. After 12 rounds of selection the binding affinity increased compared to the zero round pool. The complexity of the round 12 pool is still relatively high and rounds will continue until the resulting complexity of the pool has somewhat decreased.

TABLE 1

RBC Ghost SELEX

| SEQ ID NO: | Starting Pool | | % Y |
|---|---|---|---|
| 1 | | gggagctcagaataaacgctcaa[30N]ttcgacatgaggcccggatc | |
| | | Motif I | |
| 5 | 47/113 | gggagctcagaataaacgctcaaCTCAGTGGT----AGGTAACGGTTCAAGACGGGAttcgacatgaggcccggatc | |
| 6 | 56 | gggagctcagaataaacgctcaaCTCAGTGGT----AGGTAACGGTTATATCCGGAAttcgacatgaggcccggatc | |
| 7 | 8 | gggagctcagaataaacgctcaaAACTCAGTATA----AGGTAACGGTTCCAACCCAGAttcgacatgaggcccggatc | |
| 8 | 20/121 | gggagctcagaataaacgctcaaACTCAGTAATGCCAAGGTAACGGTTCCCTTttcgacatgaggcccggatc | |
| 9 | 117 | gggagctcagaataaacgctcaaACTCAGTAATGCT-AGGTAACGGTTCCCTTttcgacatgaggcccggatc | |
| 10 | 15 | gggagctcagaataaacgctcaaACTCAGTAATGCACCAGTAACGGTTACATCttcgacatgaggcccggatc | |
| 11 | 85/104 | gggagctcagaataaacgctcaaCTCAGTAGCA---AGGTAACGGTTCAGATCCACttcgacatgaggcccggatc | |
| 12 | 25 | agctcagaataaagcgtcaa-GTCATAACGGTTAGCCAGAGGACCGTGCCttcgacatgaggcccggatc | |
| 4 | c56t | aaCTCAGTGGT----AGGTAACGGTT | |
| 236 | c20t | aACTCAGTAATGCCAAGGTAACGGTT | |
| | | Motif II | |
| 35 | 16 | gggagctcagaataaacgctcaaACGAATCGCATTGCCCAA-CGTTGCCC-AAGAttcgacatgaggcccggatc | |
| 36 | 43 | gggagctcagaataaacgctcaaCCGAATCGCATTGCCCAA-CGTTGCCC-AAGAttcgacatgaggcccggatc | |
| 37 | 78 | gggagctcagaataaacgctcaaTGTCGGATAAGTCGCCCAA-CGTTGCCC--ATTttcgacatgaggcccggatc | |
| 22 | 79 | gggagctcagaataaacgctcaaTAG-TTGCCCA-CCGTTGTCC-AATTGATCGTAttcgacatgaggcccggatc | |
| 23 | 101 | gggagctcagaataaacgctcaaTGG-TTGCCCAT-CGTTGTCC-AATTGATCGTTttcgacatgaggcccggatc | |
| 24 | 46 | gggagctcagaataaacgctcaaT-G-TTGCCCATTCGTCGTCC-AAGTGAACGTttcgacatgaggcccggatc | |
| 25 | 66 | gggagctcagaataaacgctcaaTGAATTGCCCAA--CGTCGCCCGAA-TGATGCGttcgacatgaggcccggatc | |
| 237 | c16t | CGAATCGCATTGCCCAA-CGTTGCCC-AAGAttcg | |
| 238 | c79t | cgctcaaTAG-TTGCCCA-CCGTTGTCC-AATTGAGCG | |
| | | Motif III | |
| 18 | 11 | gggagctcagaataaacgctcaaGTGGAGTCGACACGCTGTGACCTTTG-GCATttcgacatgaggcccggatc | |
| 19 | 119 | gggagctcagaataaacgctcaaGTG-AGTCGACACGCCGCGACCTTTG-GTATttcgacatgaggcccggatc | |
| 20 | 111 | gggagctcagaataaacgctcaaGTG-CGTCGAGGCATTGCAACCTTTG-GTCTttcgacatgaggcccggatc | |
| 21 | 18 | gggagctcagaataaacgctcaaTAGACCGTCGATGC-TTGCAACTTTAC-GTATttcgacatgaggcccggatc | |
| 28 | 22 | gggagctcagaataaacgctcaaTGAGAGGGGCAACC-TTGAGTCTTTCATGCCttcgacatgaggcccggatc | |
| 29 | 53 | gggagctcagaataaacgctcaaAGCAGCGGGCAACC-TTGAGTATTTCATGCttcgacatgaggcccggatc | |
| 30 | 132 | gggagctcagaataaacgctcaaACCCGGGCAACCGTTCGGTCTTTCAGTCTttcgacatgaggcccggatc | |
| 40 | 7 | gggagctcagaataaacgctcaaCATCTGGATGTTCAACCTTCTGGTCTTGCGttcgacatgaggcccggatc | |
| 41 | 21 | gggagctcagaataaacgctcaaCTACCCGGTTGAACCTTC-GCTCTTGCGTAGttcgacatgaggcccggatc | |
| 42 | 38 | gggagctcagaataaacgctcaaTGCTCCCCGAAACCCT-ATTTCTTGCTGCTAttcgacatgaggcccggatc | |
| 239 | c111t | GTCGAGGCATTGCAACCTTTG-GTCTttcgac | |
| 240 | c53t | GGGCAACC-TTGAGTATTTCATGCttcgacatgaggcccg | |
| | | Motif IV | |
| 31 | 42 | gggagctcagaataaacgctcaaCATCG-TTGACACCCTCGT---GTGCTTCAGGTAttcgacatgaggcccggatc | |
| 32 | 57 | gggagctcagaataaacgctcaaCATCGCTTGACA-GCTGTG---CTGCTTCAGTTTttcgacatgaggcccggatc | |
| 33 | 73 | gggagctcagaataaacgctcaaGGGTGATCGAAGCCTAGGT---GAGCTTGAGCCttcgacatgaggcccggatc | |
| 34 | 105 | gggagctcagaataaacgctcaaGGGTGTCCGA-GCATCCGT----AGCTTGAGTCGTttcgacatgaggcccggatc | |
| 55 | 17 | gggagctcagaataaacgctcaaAGAGGAGTC-TTGCTG--TCCGTACACAGCTTAttcgacatgaggcccggatc | |
| | | Motif V | |
| 26 | 26 | gggagctcagaataaacgctcaaAGGCGGTGT-------TACTTCTCACGAATTGAGGAAGttcgacatgaggcccggatc | |
| 27 | 39 | gggagctcagaataaacgctcaaAG-CGTTGT-------TACTTCTCACGAATTGAGGAAGttcgacatgaggcccggatc | |
| 54 | 13 | gggagctcagaataaacgctcaaGGAGCGCGATACGTTTACTTCTGATCATGttcgacatgaggcccggatc | |
| 65 | 108 | gggagctcagaataaacgctcaaTAGGCCGGGTGAGC---TACTTCTAGTAGGGTGttcgacatgaggcccggatc | |
| 53 | 6 | gggagctcagaataaacgctcaaTAGGGGTAGGGCGCAA-TA-TTCACCGGGCCTttcgacatgaggcccggatc | |
| | | Motif VI | |
| 17 | 5 | gggagctcagaataaacgctcaaGGTTGTCGACGCATTATAGCGACATCGTCTttcgacatgaggcccggatc | |
| 16 | 58 | gggagctcagaataaacgctcaaGGCGTGTCGATGTGGAATCACAAC-CTGTCTttcgacatgaggcccggatc | |

TABLE 1-continued

RBC Ghost SELEX

| SEQ ID NO: | Starting Pool | | % Y |
|---|---|---|---|
| | | Orphans | |
| 13 | 37 | gggagctcagaataaacgctcaaCAGGTCGATCGAGTCAGGTAGGCGCCGAGAttcgacatgaggcccggatc | |
| 14 | 51 | gggagctcagaataaacgctcaaGAGGTCGATCGAGTCAGGTAGGCGCCGAGAttcgacatgaggcccggatc | |
| 15 | 131 | gggagctcagaataaacgctcaaCAGGTCGATTGAGTCAGGTAGGCGCCGAGAttcgacatgaggcccggatc | |
| 38 | 81 | gggagctcagaataaacgctcaaGTGGAGCGATTCGCGAAAATCGACTTGCATttcgacatgaggcccggatc | |
| 39 | 116 | gggagctcagaataaacgctcaaCTGGAGCGATTCGG-AAAATCGACTTGCATttcgacatgaggcccggatc | |
| 52 | 4 | gggagctcagaataaacgctcaaGTGGCCTCAAACTGCTAGGAGTAAACATGTttcgacatgaggcccggatc | |
| 56 | 24 | gggagctcagaataaacgctcaaTCCCTTGAACCATCGGTCTTGCGTTCCATGttcgacatgaggcccggatc | |
| 67 | 110 | gggagctcagaataaacgctcaaTCCGGAAAGCAACGCATACTTCGCATGTCGttcgacatgaggcccggatc | |
| 63 | 84 | gggagctcagaataaacgctcaaGGGCAATACACAACACTCTACCTCACCTCAttcgacatgaggcccggatc | |
| 66 | 109 | gggagctcagaataaacgctcaaGTTGTGATCCATTAGCGGCACCGCCTCCAttcgacatgaggcccggatc | |
| 59 | 48 | gggagctcagaataaacgctcaaGACAGCGTGATTCCTCCGCTCTGCTGCTATttcgacatgaggcccggatc | |
| 68 | 123 | gggagctcagaataaacgctcaaGTGAGCGTACCGGAGTGTGTTACCAATTAttcgacatgaggcccggatc | |
| 57 | 28 | gggagctcagaataaacgctcaaACAAGAGGGTCTTGCCGCACCATTCGGCTAttcgacatgaggcccggatc | |
| 58 | 44 | gggagctcagaataaacgctcaaACGAGTTACAGCCACCCATGCTGTCGGTGAttcgacatgaggcccggatc | |
| 60 | 60 | gggagctcagaataaacgctcaaCGGGACCTTGAGTATTCCTCATTATCGTTCttcgacatgaggcccggatc | |
| 62 | 70 | gggagctcagaataaacgctcaaAGCCGAATTAGTAGCGTATAGCGTGTTGTttcgacatgaggcccggatc | |
| 64 | 107 | gggagctcagaataaacgctcaaTCAGAGATTCTTCCCGGCTATCCCGGGTGAttcgacatgaggcccggatc | |
| 61 | 67 | gggagctcagaataaacgctcaaGTAGTGAAGCTCGTACAGAGGTATTGCGTAttcgacatgaggcccggatc | |
| 69 | 124 | gggagctcagaataaacgctcaaCACATCTGCAGACTGTACCCCACATGGCAAttcgacatgaggcccggatc | |
| 70 | 128 | gggagctcagaataaacgctcaaGAGGGCCGGGTTAGCCTTTTAAGGTTGTGTttcgacatgaggcccggatc | |
| | | Pyrimidine-rich motif | |
| 44 | 30 | gggagctcagaataaacgctcaaACCTCGTACTGCCATCTCTCCCCTCATGTCttcgacatgaggcccggatc | 77 |
| 51 | 126 | gggagctcagaataaacgctcaaCGGTTCATCTTTTCTTGTTATTTTTCCACTAttcgacatgaggcccggatc | 77 |
| 45 | 35 | gggagctcagaataaacgctcaaACACTCACGACTTTTCATCTTTCTTCCTTCttcgacatgaggcccggatc | 80 |
| 43 | 2 | gggagctcagaataaacgctcaaTGCACCTCACCTCCTTACACTTTCCTTCTTttcgacatgaggcccggatc | 83 |
| 49 | 87 | gggagctcagaataaacgctcaaACCCTACTCTCCACTCACATCTTCTTCCCCttcgacatgaggcccggatc | 83 |
| 50 | 103 | gggagctcagaataaacgctcaaTACCTCACACTCTCTTAATCTCTTCTCTTCttcgacatgaggcccggatc | 83 |
| 46 | 36 | gggagctcagaataaacgctcaaAACCCTTCTTCACTCTTCTCGCTCTCCTTTttcgacatgaggcccggatc | 87 |
| 48 | 69 | gggagctcagaataaacgctcaaGCACTTCTCACTATTCCTTCCTTCTCTCTttcgacatgaggcccggatc | 87 |
| 47 | 59 | gggagctcagaataaacgctcaaCCCTTCCAATTCCTCTTACTCCTCTCTCCTttcgacatgaggcccggatc | 90 |

TABLE 2

Glioblastoma Ligand Sequences
Sequences: (fixed regions not shown)

| Ligand NO: | Random Region | |
|---|---|---|
| GBI.1 | GGCTGCTGAGTCCAGGGGCGATAACGGGCTTTG | 74 |
| GBI.2 | GGCTGCTGAGTCCAGGGGCGATAACGGGCTTTG | 75 |
| GBI.120 | GGCTGCTGAGTCCAGGGGCGATAACGAGCTTTC | 76 |
| GBI.140 | GGCTGCTGAGGCCAGGGGCGATAACCGCACTTT | 77 |
| GBI.162 | GGCTGCTGAGTCCAGGGGCGATAACGGCCTTTC | 78 |
| GBI.4 | TAGC GAACACAGGGGNCCACAACTGGCTATCTCT | 79 |
| GBI.8 | TAGCAGAACACAGGGGNCCACAACTGGCTATCTC | 80 |
| GBI.33 | TAGGCGAACACAGGGGTCCACAACTGGCTATCCC | 81 |
| GBI.124 | TAGC GAACACAGGG TCAACAGCTCACACGGCC | 82 |
| GBI.125 | TAGC GAACGARCGGTGCCCTGCTCTCAACTGGTTT | 83 |
| GBI.99 | TAGGCCGGAGGGACTAATAGCTTACAGCGCACTA | 84 |
| GBI.76 | TAGGCCGGAGGGACTAATAGCTTACAAGGCACTA | 85 |
| GBI.42 | TAGGAGCGCGAACAACGGGGAGGTCTCACACTG | 86 |
| GBI.23 | TAGGGGGNGNNATACAACAGGTCGGTCACAACTG | 87 |
| GBI.75 | TAGGGCGGAGNGNGGCGGTCATCCTGGNNACACTC | 88 |
| GBI.27 | AGGCAGAAGTGAGCTTGGGCTCGCAACTCTCTCC | 89 |
| GBI.29 | AGGCNGTAG GNGCTAGGGNGNACTCGTATTCCTC | 90 |
| GBI.101 | AGGCAGCAGTGA CTTGGA CGACAACAGCTATGTC | 91 |
| GBI.156 | AGGCAGTAGTGA CTTGGGCGCAGAGGAGGGTAGT | 92 |
| GBI.189 | AGGGCGCAGGG TCTAGGGCANCCAACAGCTATTG | 93 |
| GBI.145 | AGGCGAAGGGN  CTAGGGTGNACAGCAGCGGTGG | 94 |
| GBI.10 | NNNAGAGGGAAGACTTTAGGTTCGGTTCACGTCC | 95 |
| GBI.36 | NNNAGAGGGAAGAC TTAGGTTCGGTTCACGTCC | 96 |
| GBI.41 | CCCAGAGGGAAGACTTTAGGTTCGGTTCACGTCCC | 97 |
| GBI.73 | NCCAGAGGGNAGACTTTAGGTTCGGTTCACGTCC | 98 |
| GBI.132 | NNNAGAGGGAAGGCTTTAGGTTCGGTTCACGTCC | 99 |
| GBI.170 | NNNAGAGGGAAGACTTTAGGTTCGGTTCACGTTC | 100 |
| GBI.181 | NNNAGGGGNAGACTTTAGGTTCGGTTCACGTCC | 101 |

TABLE 2-continued

Glioblastoma Ligand Sequences
Sequences:(fixed regions not shown)

| Ligand NO: | Random Region | |
|---|---|---|
| GBI.14 | GTGTGCAACAGAGCAGNNNTTGTCTAACATCACTT | 102 |
| GBI.13 | GGGGCGAACAGCAGCTACTCACAACATGTCCGGC | 103 |
| GBI.26 | GTGGCGAACACGGGTCAAGGGCTTCACAATCTG | 104 |
| GBI.35 | ATGGCGAACACAGCAACTCGCTCACAACTCTCTCC | 105 |
| GBI.38 | GTAGGCGAACACAGGTTGAGGCTTACACAGGGNT | 106 |
| GBI.43 | AGCGAACAACTGACTGACGGCAGGGTCAACACNNC | 107 |
| GBI.52 | TACGAACAACAGCATTCACACAGGCCTTTTTGTT | 108 |
| GBI.183 | AGCGAGCAACATCTTTCGCAACAGGTTTGGTTCC | 109 |
| GBI.62 | TTGGCGAACACAGCAACTCGCTCACAACTATCTT | 110 |
| GBI.6 | AGGTTGGGTAGGTTGG TGGAGGCGAACGTACCAA | 111 |
| GBI.58 | AGGTTGGGTAGGTTGG TGGAGGCGAACGTCCTAA | 112 |
| GBI.182 | AGGTTGGGTAGGCTGG TGGAGGCGNACGTCCCAT | 113 |
| GBI.141 | AGGTTCGC AGGCTGGCTGGAGGCGCGCGACCCAA | 114 |
| GBI.37 | GGTTTGACCG TAACAA TTGTTAAA GCTCCGGGNN | 115 |
| GBI.61 | GGTCTGATCG TAACAA TTGTTAAA GCTCCGGGNC | 116 |
| GBI.86 | GGTTTGATCTCTAACAA TTGTTAAA GCTCCAGGC | 117 |
| GBI.94 | GGTCTGATCGCTAACAA TTGTTAAA GCTCCGGGGC | 118 |
| GBI.104 | GGTCTGATCG TAACAAATTGTTAAAAGCTCCGGGCC | 119 |
| GBI.119 | GGTTTG TCG TAACAA TTGTTAAA GCTCCGGGAC | 120 |
| GBI.171 | GGTCTGATCG TAACAG TTGTTAAAAGCTCCGGGCG | 121 |
| GBI.187 | GGTCTGATCG TAACAA TTGTTAA GCTCCGGGCG | 122 |
| GBI.18 | CCGCCAAGGGAGCTCTCCGAGCTCGGCGCCACTC | 123 |
| GBI.60 | NCNNCNAAGGAAGATCTCCGAGTTCGGCGTCACTG | 124 |
| GBI.68 | CTGCCGGGGAAGATCTCCGAGTTCGGCGTCACTG | 125 |
| GBI.69 | CCGCCAAGGAAGATCTCCGAGTTCGGCGTCACTG | 126 |
| GBI.89 | CNGCNAAGGAAGATCTCCGAGTTCGGCGTCACTG | 127 |
| GBI.123 | CNGCCAAGGAAGATCTCCGAGTTCGGCGTCACTA | 128 |
| GBI.185 | CNNCNAAGGAAGATCTCC AGTTCGGCGTCACTG | 129 |
| GBI.188 | CNGCNAAGGAAGATCTCCGAGTTCGGNGTTACTG | 130 |
| GBI.16 | AGACCGTAGGG TTCGGGAGCGATAAACAGTCGTT | 131 |
| GBI.126 | AGACCGTAGGGGCTTGGGCCA TCAACTGGCGCGG | 132 |
| GBI.114 | AGACGGTAGCGCCTTGAGTGAATCAATCAGNAGTAA | 133 |
| GBI.129 | AGACCGTTGGGACTATA GGCGAACACCAGCTACCA | 134 |
| GBI.164 | AGACGGTAGCCC TTAACGGCGAACAACGCGTTT | 135 |
| GBI.70 | AGACTGT AGAGACTTGATGGGTCGCAACCGTCA | 136 |
| GBI.79 | AGACTGT AGAGGCTA GGGTAACAACGGCTCGTTT | 137 |
| GBI.90 | AGACTGTGAGAGACTA GGCGAGAAACGGGGTTCTC | 138 |
| GBI.130 | AGACTGT AGAGGCTA GGGCATCAACAGTTCTTCC | 139 |
| GBI.154 | AGACTG GAGAGACTA GGCGAGAACCGGGGCGC | 140 |
| GBI.22 | AGAGAGGAGAACTTAT AGGAAACAACGGTCGGC | 141 |
| GBI.157 | AGACTGTAGAGGCTA GGGTAACAACGGCTCGTCTG | 142 |
| GBI.158 | AGACTGTTGAGACTAACTGCGAACAACTGC TGTA | 143 |
| GBI.190 | AGAGCTGTTGACACTAACGCGAACAACAAC TGTA | 144 |
| GBI.66 | TGGAGGCGATACTTGGCGAACAACAGGGGCTGTA | 145 |
| GBI.74 | ATGCCGAACAACAGTCTGAACAACAGGTC TGTAT | 146 |
| GBI.107 | TAGAGCGAATACTTGGCGGAACAACAGGGC TGTA | 147 |
| GBI.178 | GGACTGTAGAGACCAGTGGAACAACAGATCG GTA | 148 |
| GBI.118 | TGGAGGCGAA TCTGGCGAGACAACAGCTTTATCTC | 149 |
| GBI.137 | TGGAGGCGAAGTCTGGCGA ACAAGCGCTTTATCTC | 150 |
| GBI.142 | TGGAGGCGAA TCTGTCGA ACAACACGTTTATCCC | 151 |
| GBI.32 | GT CGGAGNAAACTATGTGTTTTAGAGCCATCCC | 152 |
| GBI.167 | GTACGGAGAAAACTATGTGTTTTAGAGCCATCCC | 153 |
| GBI.184 | GTACGGCGCAAACAATGTGTTTTAGAGCNACTCC | 154 |
| GBI.34 | GTGTAGACTGCAGAGACTGCCAGTGATCTCTCCC | 155 |
| GBI.45 | GTGTAGACTGCAGAGACTGCCAGTGCTCTCTCCC | 156 |
| GBI.72 | TTGGGGCGAACACAGGTTGAGGCTTACACAGGGTT | 157 |
| GBI.102 | AGTAGGCGNACACAGGTTGAGGCTTACACAGGGTT | 158 |
| GBI.49 | GAACAGGCNNN TTACCTCTGTGGCCGTTTATCCCTC | 159 |
| GBI.67 | CAGCCCNCCTTACCTCTGT GCAGTTTATCCCTCT | 160 |
| GBI.9 | AGACATGGACACTAGGGGACACTGCAGCCAACTT | 161 |
| GBI.31 | AGACA GGAGTGACTTGGCAGCTNACAGACGCTTC | 162 |
| GBI.95 | GAGACA GGACTGACTTGGCAGCTCACAG CGCTTC | 163 |
| GBI.11 | TAGTGGCGAACGACAGACTCTCACACACACAGGCTTG | 164 |
| GBI.19 | TAAGTGGCGAACGACAG CTCTCACACACA GGCTTG | 165 |
| GBI.3 | TAGTTCCTTGCTTATTCTTGCTTCCCTTGTCTG | 166 |
| GBI.5 | AGCACTGAGATACGCTTATTCTTGTCTCCGGGCTTGT | 167 |
| GBI.15 | GAGGACGATCAACAGCGACTTATTCTCACAACTG | 168 |
| GBI.17 | TCCCGCTTATTCTTGTCTCAGCTTATTATTCTTGT | 169 |
| GBI.40 | GTGGNNNAAATTCNCTTATTCTTGTCTCTCGTGGT | 170 |
| GBI.50 | ACCAGTACGATTATTCTTGTCTCCCTGNNTTNNNT | 171 |
| GBI.59 | GGTGGTTGAGCTTATTCTTGTCTCGATTTGCACGTGT | 172 |
| GBI.78 | ACCTTGCGGCTTATTCTTGTCTCGCTTCTTCTTGT | 173 |
| GBI.80 | AGTTGTTGTCCGCGTTTCTTGTCTCCCTTTTCCT | 174 |

TABLE 2-continued

Glioblastoma Ligand Sequences
Sequences: (fixed regions not shown)

| Ligand NO: | Random Region | |
|---|---|---|
| GBI.81 | TAGTCCCTTGCTTATTCTTGTCTTCCCTTGTCTG | 175 |
| GBI.82 | ACCTTCCGGCTTATTCTTGTTCTCTGCTTATTCTTGT | 176 |
| GBI.85 | GTCGCTTATTCTTGTCTCCCTCTTATTCTTGTCCC | 177 |
| GBI.103 | AGCACGAGATACGCTTATTCTTGTCTCCGCGCTTCT | 178 |
| GBI.108 | TGTGTTGTTGTTCTTTGTGTCATCCCTGTTCCTC | 179 |
| GBI.111 | TAGTGCCTGGGACGCTTATTCTTGTCTCCGGGNCTA | 180 |
| GBI.39 | GGAGGCGCTTGTGTCTTGTTCCCTTGTGTGTCTC | 181 |
| GBI.163 | GTGGGGTTGTTGTCTTATTCTTGTCTCCGG | 182 |
| GBI.166 | AGTCCCCGCTTATTCTTGTCTCCCTTATCGCG | 183 |
| GBI.169 | ACACGCTTATTCTTGTCTCCACTTATTCTTGT | 184 |
| GBI.174 | GTTGTCGCTTATTCTTGTCTCTGTCTGTTTTGTC | 185 |
| GBI.177 | AGAGTGGGGGGCGCTTATTCTTGTCTCCACTCGCTTGT | 186 |
| GBI.179 | GACACCCGCCGCGCTTATTGTTGTCTCCNNNCTTTC | 187 |
| GBI.191 | GTTGTCGCTTATTCTTGTCTCCCATCCTCTACTC | 188 |
| GBI.180 | AGCCGTGTCCAGCTTATTCTTGTCTCCTNNCTTC | 189 |
| GBI.24 | GGTTGTGTGACTTCTATTTGNNTTTCGTGTCCC | 190 |
| GBI.51 | GTCGCTGTGTACCGTTTTTTTCTTGTTTGCCTGTC | 191 |
| GBI.71 | GGTAGGTCCTTTTCTGTCTTCCTTGTTCTCTCGC | 192 |
| GBI.77 | TGTCTGTCCGTTCTTTTTGTCTGTGTTTTCCCN | 193 |
| GBI.83 | GTACCTGTTGTCAGCTTTTACCCTTCGTTCCTC | 194 |
| GBI.87 | AGTCGCGATTCTATTTTTCACTTTCTGTTGTTGC | 195 |
| GBI.88 | GTTGCCGTATCCTTGTGGAGTTTTCGTTTCTCCC | 196 |
| GBI.91 | GTTGGTCNGTTCCTTTCTCTGTTGTTCTCCTC | 197 |
| GBI.190 | TAGTCCCGCGGCTTATTTTTGTCTCCGTTCCGTT | 198 |
| GBI.115 | AGTCCCTCNNNNATCCTTTTGTTGTCTTGCTGTC | 199 |
| GBI.116 | TGTGTGTGTCGGTGGTTTTTGTCTTCCTTTTGC | 200 |
| GBI.117 | GTGTCCGTTGTTCGCGTTTTGTGNCCTGTTTTTCC | 201 |
| GBI.133 | AGAAGCCTTGTCGTCTTTCCGTTTCTTCTTGT | 202 |
| GBI.186 | ACCGGTAGGAGTCCGTTTTTGTTTGCACTATGCC | 203 |
| GBI.175 | ACCCNACTGTGATGTTCGTGTTTTGTTCCTCCNC | 204 |
| GBI.20 | GGTCACACCAGTCACAGCACCTACGTCCTGCCCTC | 205 |
| GBI.21 | GTAGTGGAACCGACTAGCGGGGTGAAGACTCCTC | 206 |
| GBI.25 | TAGCCCACAGCAATTTTAGTCTGAGTTCCGTC | 207 |
| GBI.30 | AGGCTGCCGTAAGCTTTGGGAATTGGCCTGCTGC | 208 |
| GBI.53 | TGGAGGCGAATCTGGCGAACAACAGCCTTATCTC | 209 |
| GBI.54 | GAGGCTGTAGAGGCTGACTGCGCGCAGCTGCTGTG | 210 |
| GBI.57 | GAGGCGAGACAGGGTAGCACCTCACAACATGC | 211 |
| GBI.65 | TGGACTGGAGAGACCTTAGGAGTCATAACTCTCTC | 212 |
| GBI.98 | GACTGAAGAGCTCAGAGGCGATACAGGCCGCTGT | 213 |
| GBI.106 | AAGACAGCAGTGGCTAGGGCGATAACTGTCACCAC | 214 |
| GBI.110 | GACCGCAGGGTTCGGGAGCGATAAACTAGACCTT | 215 |
| GBI.112 | CATGCGGGTTTGTCCGGACCTCAGCAACAGCTAC | 216 |
| GBI.113 | GAAGGCGNANACAGGAGGAAAGGCTNACACCTATC | 217 |
| GBI.121 | GACTGTAGAGACAGGACGTACAATAGGCTCACTC | 218 |
| GBI.122 | GTTGCATTCCAGGACCGTTCTGTCNGTACCTCGCGC | 219 |
| GBI.127 | ATGGGGCGAACCTTTGCGCTCACAACCTACCTGC | 220 |
| GBI.128 | GAACGACGGGACAGGGCTGAAAACAGGCAGCTAC | 221 |
| GBI.131 | TGCGCGGTGTTGCNCTTTGTTCTATTCTCCTGTC | 222 |
| GBI.135 | TGAACCACAAGCCCCAACTAACAACACCCTGC | 223 |
| GBI.143 | AGGGTGAGATCCAGGGCGCGCTACGTGCGTGTC | 224 |
| GBI.147 | ACCGCGACTCTTTGCGTACTTCTTGGTCTTCCGCCT | 225 |
| GBI.151 | TGGGCGAAGGGTCTTGGACGAGGACAGGCGC | 226 |
| GBI.165 | AGGTCACCGTTATCTCTTCCTGTTGCTCTTTCGC | 227 |
| GBI.168 | AGTCAAACCCCTCTACGCTGTTGTTGATGTCTCCC | 228 |
| GBI.172 | TAGGCAGAACTCACTAAAAGGTCCAACTGGTTCC | 229 |
| GBI.173 | TGGACAGGACTCACCTACAAGGCTTACAACGCAT | 230 |
| GBI.176 | GTAGACTGTAGAGTTACGGCGCGACTACAACGCT | 231 |
| GBI.192 | AGGCGGTAGCTACTAACATATCACAACATCTTAC | 232 |

What is claimed is:

1. A nucleic acid ligand to a cell target macromolecule identified according to the method comprising:
   a) preparing a candidate mixture of nucleic acid sequences;
   b) contacting said candidate mixture of nucleic acids with said cell, wherein nucleic acids having an increased affinity to the cell macromolecule relative to the candidate mixture may be partitioned from the remainder of the candidate mixture;
   c) partitioning the increased affinity nucleic acids from the remainder of the candidate mixture; and
   d) optionally amplifying the increased affinity nucleic acids to yield a mixture of nucleic acids enriched for nucleic acid sequences with relatively higher affinity and specificity for binding to said cell,
   whereby said nucleic acid ligand to said macromolecule may be identified.

2. A purified and isolated non-naturally occuring nucleic acid ligand to a cell macromolecule.

3. The purified nucleic acid ligand of claim 2 which is a non-naturally occurring nucleic acid ligand having a specific binding affinity for the cell target macromolecule, said macromolecule being a three dimensional chemical structure other than a polynucleotide that binds to said nucleic acid ligand through a mechanism which predominantly depends on Watson/Crick base pairing or triple helix binding, wherein said nucleic acid ligand is not a nucleic acid having the known physiological function of being bound by the target molecule.

4. The nucleic acid ligand of claim 2 which is a deoxyribonucleic acid ligand.

5. The nucleic acid ligand of claim 2 which is a ribonucleic acid ligand.

6. A method of purifying macromolecule component of a cell comprising:
   a) identifying a nucleic acid ligand to said macromolecule according to the method comprising:
      i) preparing a candidate mixture of nucleic acid sequences;
      ii) contacting said candidate mixture of nucleic acids with said cell, wherein nucleic acids having an increased affinity to the cell macromolecule relative to the candidate mixture may be partitioned from the remainder of the candidate mixture;
      iii) partitioning the increased affinity nucleic acids from the remainder of the candidate mixture; and
      iv) optionally amplifying the increased affinity nucleic acids to yield a mixture of nucleic acids enriched for nucleic acid sequences with relatively higher affinity and specificity for binding to said cell
      whereby said nucleic acid ligand to said macromolecule may be identified;
   b) separating said macromolecule component of said cell away from the remainder of said cell on the basis of affinity between said cell macromolecule and said nucleic acid ligand; and
   c) purifying said macromolecule.

7. The method of claim 6 wherein said macromolecule is selected from the group consisting of a protein, lipid and carbohydrate.

8. A purified macromolecule identified according to the method of claim 6.

9. The purified macromolecule of claim 8 which is selected from the group consisting of a protein, lipid and carbohydrate.

10. The purified macromolecule of claim 9 which is a tumor associated antigen.

* * * * *

SEQUENCE LISTING (1) GENERAL INFORMATION:

(iii) NUMBER OF SEQUENCES: 240

(2) INFORMATION FOR SEQ ID NO:1:

(i) SEQUENCE CHARACTERISTICS:
    (A) LENGTH: 73 base pairs
    (B) TYPE: nucleic acid
    (C) STRANDEDNESS: single
    (D) TOPOLOGY: linear (xi) SEQUENCE DESCRIPTION: SEQ ID NO:1:

GGGAGCTCAG AATAAACGCT CAANNNNNNN NNNNNNNNNN NNNNNNNNNN        50

NNNTTCGACA TGAGGCCCGG ATC        73

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:2:

GGGAGCTCAG AATAAACGCT CAA        23

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:3:

GATCCGGGCC TCATGTCGAA        20

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:4:

AACTCAGTGG TAGGTAACGG TT        22

(2) INFORMATION FOR SEQ ID NO:5:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:5:

GGGAGCTCAG AATAAACGCT CAACTCAGTG GTAGGTAACG GTTCAAGACG        50

GGATTCGACA TGAGGCCCGG ATC        73

(2) INFORMATION FOR SEQ ID NO:6:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:6:

GGGAGCTCAG AATAAACGCT CAACTCAGTG GTAGGTAACG GTTATATCCG        50

```
GAATTCGACA TGAGGCCCGG ATC                                                    73

(2) INFORMATION FOR SEQ ID NO:7:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:7:

GGGAGCTCAG AATAAACGCT CAAAACTCAG TATAAGGTAA CGGTTCCAAC                        50

CCAGATTCGA CATGAGGCCC GGATC                                                  75

(2) INFORMATION FOR SEQ ID NO:8:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:8:

GGGAGCTCAG AATAAACGCT CAAACTCAGT AATGCCAAGG TAACGGTTCC                        50

CTTTTCGACA TGAGGCCCGG ATC                                                    73

(2) INFORMATION FOR SEQ ID NO:9:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:9:

GGGAGCTCAG AATAAACGCT CAAACTCAGT AATGCTAGGT AACGTTCCC                         50

TTTTCGACAT GAGGCCCGGA TC                                                     72

(2) INFORMATION FOR SEQ ID NO:10:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:10:

GGGAGCTCAG AATAAACGCT CAAACTCAGT AATGCACCAG TAACGGTTAC                        50

ATCTTCGACA TGAGGCCCGG ATC                                                    73

(2) INFORMATION FOR SEQ ID NO:11:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:11:

GGGAGCTCAG AATAAACGCT CAACTCAGTA GCAAGGTAAC GGTTCAGATC                        50

CACTTCGACA TGAGGCCCGG ATC                                                    73
```

```
(2) INFORMATION FOR SEQ ID NO:12:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:12:

GGGAGCTCAG AATAAACGCT CAAGTCATAA CGGTTAGCCA GAGGACCGTG          50

CCTTCGACAT GAGGCCCGGA TC                                       72

(2) INFORMATION FOR SEQ ID NO:13:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:13:

GGGAGCTCAG AATAAACGCT CAACAGGTCG ATCGAGTCAG GTAGGCGCCG          50

AGATTCGACA TGAGGCCCGG ATC                                      73

(2) INFORMATION FOR SEQ ID NO:14:

(i) SEQUENCE CHARACTERISTICS:
        (A) LENGTH: 73 base pairs
        (B) TYPE: nucleic acid
        (C) STRANDEDNESS: single
        (D) TOPOLOGY:linear (xi) SEQUENCE DESCRIPTION: SEQ ID NO:14:

GGGAGCTCAG AATAAACGCT CAAGAGGTCG ATCGAGTCAG GTAGGCGCCG          50

AGATTCGACA TGAGGCCCGG ATC                                      73

(2) INFORMATION FOR SEQ ID NO:15:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:15:

GGGAGCTCAG AATAAACGCT CAACAGGTCG ATTGAGTCAG GTAGGCGCCG          50

AGATTCGACA TGAGGCCCGG ATC                                      73

(2) INFORMATION FOR SEQ ID NO:16:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:16:

GGGAGCTCAG AATAAACGCT CAAGGCGTGT CGATGTGGAA TCACAACCTG          50

TCTTTCGACA TGAGGCCCGG ATC                                      73

(2) INFORMATION FOR SEQ ID NO:17:

(i) SEQUENCE CHARACTERISTICS:
        (A) LENGTH: 73 base pairs
```

(B) TYPE: nucleic acid
            (C) STRANDEDNESS: single
            (D) TOPOLOGY: linear (xi) SEQUENCE DESCRIPTION: SEQ ID NO:17:

GGGAGCTCAG AATAAACGCT CAAGGTTGTC GACGCATTAT AGCGACATCG          50

TCTTTCGACA TGAGGCCCGG ATC                                      73

(2) INFORMATION FOR SEQ ID NO:18:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (xi) SEQUENCE DESCRIPTION: SEQ ID NO:18:

GGGAGCTCAG AATAAACGCT CAAGTGGAGT CGACACGCTG TGACCTTTGG          50

CATTTCGACA TGAGGCCCGG ATC                                      73

(2) INFORMATION FOR SEQ ID NO:19:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (xi) SEQUENCE DESCRIPTION: SEQ ID NO:19:

GGGAGCTCAG AATAAACGCT CAAGTGAGTC GACACGCCGC GACCTTTGGT          50

ATTTCGACAT GAGGCCCGGA TC                                       72

(2) INFORMATION FOR SEQ ID NO:20:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (xi) SEQUENCE DESCRIPTION: SEQ ID NO:20:

GGGAGCTCAG AATAAACGCT CAAGTGCGTC GAGGCATTGC AACCTTTGGT          50

CTTTCGACAT GAGGCCCGGA TC                                       72

(2) INFORMATION FOR SEQ ID NO:21:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (xi) SEQUENCE DESCRIPTION: SEQ ID NO:21:

GGGAGCTCAG AATAAACGCT CAATAGACCG TCGATGCTTG CAACTTTACG          50

TATTTCGACA TGAGGCCCGG ATC                                      73

(2) INFORMATION FOR SEQ ID NO:22:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (xi) SEQUENCE DESCRIPTION: SEQ ID NO:22:

GGGAGCTCAG AATAAACGCT CAATAGTTGC CCACCGTTGT CCAATTGATC            50

GTATTCGACA TGAGGCCCGG ATC            73

(2) INFORMATION FOR SEQ ID NO:23:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (xi) SEQUENCE DESCRIPTION: SEQ ID NO:23:

GGGAGCTCAG AATAAACGCT CAATGGTTGC CCATCGTTGT CCAATTGATC            50

GTTTTCGACA TGAGGCCCGG ATC            73

(2) INFORMATION FOR SEQ ID NO:24:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (xi) SEQUENCE DESCRIPTION: SEQ ID NO:24:

GGGAGCTCAG AATAAACGCT CAATGTTGCC CATTCGTCGT CCAAGTGAAC            50

GTTTCGACAT GAGGCCCGGA TC            72

(2) INFORMATION FOR SEQ ID NO:25:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (xi) SEQUENCE DESCRIPTION: SEQ ID NO:25:

GGGAGCTCAG AATAAACGCT CAATGAATTG CCCAACGTCG CCCGAATGAT            50

GCGTTCGACA TGAGGCCCGG ATC            73

(2) INFORMATION FOR SEQ ID NO:26:

(i) SEQUENCE CHARACTERISTICS:
            (A) LENGTH: 74 base pairs
            (B) TYPE: nucleic acid
            (C) STRANDEDNESS: single
            (D) TOPOLOGY: linear (xi) SEQUENCE DESCRIPTION: SEQ ID NO:26:

GGGAGCTCAG AATAAACGCT CAAAGGCGGT GTTACTTCTC ACGAATTGAG            50

GAAGTTCGAC ATGAGGCCCG GATC            74

(2) INFORMATION FOR SEQ ID NO:27:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (xi) SEQUENCE DESCRIPTION: SEQ ID NO:27:

GGGAGCTCAG AATAAACGCT CAAAGCGTTG TTACTTCTCA CGAATTGAGG            50

AAGTTCGACA TGAGGCCCGG ATC                                                   73

(2) INFORMATION FOR SEQ ID NO:28:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:28:

GGGAGCTCAG AATAAACGCT CAATGAGAGG GGCAACCTTG AGTCTTTCAT                      50

GCCTTCGACA TGAGGCCCGG ATC                                                   73

(2) INFORMATION FOR SEQ ID NO:29:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:29:

GGGAGCTCAG AATAAACGCT CAAAGCAGCG GGCAACCTTG AGTATTTCAT                      50

GCTTCGACAT GAGGCCCGGA TC                                                    72

(2) INFORMATION FOR SEQ ID NO:30:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:30:

GGGAGCTCAG AATAAACGCT CAAACCCGGG CAACCGTTCG GTCTTTCAGT                      50

CTTTCGACAT GAGGCCCGGA TC                                                    72

(2) INFORMATION FOR SEQ ID NO:31:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:31:

GGGAGCTCAG AATAAACGCT CAACATCGTT GACACCCTCG TGTGCTTCAG                      50

GTATTCGACA TGAGGCCCGG ATC                                                   73

(2) INFORMATION FOR SEQ ID NO:32:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:32:

GGGAGCTCAG AATAAACGCT CAACATCGCT TGACAGCTGT GCTGCTTCAG                      50

TTTTTCGACA TGAGGCCCGG ATC                                                   73

(2) INFORMATION FOR SEQ ID NO:33:

(i) SEQUENCE CHARACTERISTICS:
    (A) LENGTH: 73 base pairs
    (B) TYPE: nucleic acid
    (C) STRANDEDNESS: single
    (D) TOPOLOGY: linear (xi) SEQUENCE DESCRIPTION: SEQ ID NO:33:

GGGAGCTCAG AATAAACGCT CAAGGGTGAT CGAAGCCTAG GTGAGCTTGA         50

GCCTTCGACA TGAGGCCCGG ATC                                     73

(2) INFORMATION FOR SEQ ID NO:34:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:34:

GGGAGCTCAG AATAAACGCT CAAGGGTGTC CGAGCATCCG TAGCTTGAGT         50

CGTTTCGACA TGAGGCCCGG ATC                                     73

(2) INFORMATION FOR SEQ ID NO:35:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:35:

GGGAGCTCAG AATAAACGCT CAAACGAATC GCATTGCCCA ACGTTGCCCA         50

AGATTCGACA TGAGGCCCGG ATC                                     73

(2) INFORMATION FOR SEQ ID NO:36:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:36:

GGGAGCTCAG AATAAACGCT CAACCGAATC GCATTGCCCA ACGTTGCCCA         50

AGATTCGACA TGAGGCCCGG ATC                                     73

(2) INFORMATION FOR SEQ ID NO:37:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:37:

GGGAGCTCAG AATAAACGCT CAATGTCGGA TAAGTCGCCC AACGTTGCCC         50

ATTTTCGACA TGAGGCCCGG ATC                                     73

(2) INFORMATION FOR SEQ ID NO:38:

(i) SEQUENCE CHARACTERISTICS:
        (A) LENGTH: 73 base pairs
        (B) TYPE: nucleic acid (C) STRANDEDNESS: single
            (D) TOPOLOGY: linear (xi) SEQUENCE DESCRIPTION: SEQ ID NO:38:

GGGAGCTCAG AATAAACGCT CAAGTGGAGC GATTCGCGAA AATCGACTTG         50

CATTTCGACA TGAGGCCCGG ATC         73

(2) INFORMATION FOR SEQ ID NO:39:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (xi) SEQUENCE DESCRIPTION: SEQ ID NO:39:

GGGAGCTCAG AATAAACGCT CAACTGGAGC GATTCGGAAA ATCGACTTGC         50

ATTTCGACAT GAGGCCCGGA TC         72

(2) INFORMATION FOR SEQ ID NO:40:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (xi) SEQUENCE DESCRIPTION: SEQ ID NO:40:

GGGAGCTCAG AATAAACGCT CAACATCTGG ATGTTCAACC TTCTGGTCTT         50

GCGTTCGACA TGAGGCCCGG ATC         73

(2) INFORMATION FOR SEQ ID NO:41:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (xi) SEQUENCE DESCRIPTION: SEQ ID NO:41:

GGGAGCTCAG AATAAACGCT CAACTACCCG GTTGAACCTT CGCTCTTGCG         50

TAGTTCGACA TGAGGCCCGG ATC         73

(2) INFORMATION FOR SEQ ID NO:42:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (xi) SEQUENCE DESCRIPTION: SEQ ID NO:42:

GGGAGCTCAG AATAAACGCT CAATGCTCCC CGAAACCCTA TTTCTTGCTG         50

CTATTCGACA TGAGGCCCGG ATC         73

(2) INFORMATION FOR SEQ ID NO:43:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (xi) SEQUENCE DESCRIPTION: SEQ ID NO:43:

```
GGGAGCTCAG AATAAACGCT CAATGCACCT CACCTCCTTA CACTTTCCTT          50

CTTTTCGACA TGAGGCCCGG ATC                                      73

(2) INFORMATION FOR SEQ ID NO:44:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:44:

GGGAGCTCAG AATAAACGCT CAAACCTCGT ACTGCCATCT CTCCCCTCAT          50

GTCTTCGACA TGAGGCCCGG ATC                                      73

(2) INFORMATION FOR SEQ ID NO:45:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:45:

GGGAGCTCAG AATAAACGCT CAAACACTCA CGACTTTTCA TCTTTCTCCT          50

TCTTTCGACA TGAGGCCCGG ATC                                      73

(2) INFORMATION FOR SEQ ID NO:46:

(i) SEQUENCE CHARACTERISTICS:
        (A) LENGTH:  73 base pairs
        (B) TYPE: nucleic acid
        (C) STRANDEDNESS: single
        (D) TOPOLOGY: linear (xi) SEQUENCE DESCRIPTION: SEQ ID NO:46:

GGGAGCTCAG AATAAACGCT CAAAACCCTT CTTCACTCTT CTCGCTCTCC          50

TTTTTCGACA TGAGGCCCGG ATC                                      73

(2) INFORMATION FOR SEQ ID NO:47:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:47:

GGGAGCTCAG AATAAACGCT CAACCCTTCC AATTCCTCTT ACTCCTCTCT          50

CCTTTCGACA TGAGGCCCGG ATC                                      73

(2) INFORMATION FOR SEQ ID NO:48:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:48:

GGGAGCTCAG AATAAACGCT CAAGCACTTC TCACTATTCC TTCCTTCTCT          50

CTCTTCGACA TGAGGCCCGG ATC                                      73
```

(2) INFORMATION FOR SEQ ID NO:49:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:49:

```
GGGAGCTCAG AATAAACGCT CAAACCCTAC TCTCCACTCA CATCTTCTTC          50

CCCTTCGACA TGAGGCCCGG ATC                                      73
```

(2) INFORMATION FOR SEQ ID NO:50:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:50:

```
GGGAGCTCAG AATAAACGCT CAATACCTCA CACTCTCTTA ATCTCTTCTC          50

TTCTTCGACA TGAGGCCCGG ATC                                      73
```

(2) INFORMATION FOR SEQ ID NO:51:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (xi) SEQUENCE DESCRIPTION: SEQ ID NO:51:

```
GGGAGCTCAG AATAAACGCT CAACGGTTCA TCTTTTCTTG TTATTTTTCC          50

ACTATTCGAC ATGAGGCCCG GATC                                     74
```

(2) INFORMATION FOR SEQ ID NO:52:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:52:

```
GGGAGCTCAG AATAAACGCT CAAGTGGCCT CAAACTGCTA GGAGTAAACA          50

TGTTTCGACA TGAGGCCCGG ATC                                      73
```

(2) INFORMATION FOR SEQ ID NO:53:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:53:

```
GGGAGCTCAG AATAAACGCT CAATAGGGGT AGGGCGCAAT ATTCACCGGG          50

CCTTCGACAT GAGGCCCGGA TC                                       72
```

(2) INFORMATION FOR SEQ ID NO:54:

(i) SEQUENCE CHARACTERISTICS:
    (A) LENGTH: 72 base pairs
    (B) TYPE: nucleic acid
    (C) STRANDEDNESS: single
    (D) TOPOLOGY: linear (xi) SEQUENCE DESCRIPTION: SEQ ID NO:54:

GGGAGCTCAG AATAAACGCT CAAGGAGCGC GATACGTTTA CTTCTGATCA           50

TGTTCGACAT GAGGCCCGGA TC                                        72

(2) INFORMATION FOR SEQ ID NO:55:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:55:

GGGAGCTCAG AATAAACGCT CAAAGAGGAG TCTTGCTGTC CGTACACAGC           50

TTATTCGACA TGAGGCCCGG ATC                                        73

(2) INFORMATION FOR SEQ ID NO:56:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:56:

GGGAGCTCAG AATAAACGCT CAATCCCTTG AACCATCGGT CTTGCGTTCC           50

ATGTTCGACA TGAGGCCCGG ATC                                        73

(2) INFORMATION FOR SEQ ID NO:57:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:57:

GGGAGCTCAG AATAAACGCT CAAACAAGAG GGTCTTGCCG CACCATTCGG           50

CTATTCGACA TGAGGCCCGG ATC                                        73

(2) INFORMATION FOR SEQ ID NO:58:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:58:

GGGAGCTCAG AATAAACGCT CAAACGAGTT ACAGCCACCC ATGCTGTCGG           50

TGATTCGACA TGAGGCCCGG ATC                                        73

(2) INFORMATION FOR SEQ ID NO:59:

(i) SEQUENCE CHARACTERISTICS:
        (A) LENGTH: 73 base pairs
        (B) TYPE: nucleic acid
        (C) STRANDEDNESS: single (D) TOPOLOGY: linear (xi) SEQUENCE DESCRIPTION: SEQ ID NO:59:

GGGAGCTCAG AATAAACGCT CAAGACAGCG TGATTCCTCC GCTCTGCTGC         50

TATTTCGACA TGAGGCCCGG ATC                                     73

(2) INFORMATION FOR SEQ ID NO:60:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:60:

GGGAGCTCAG AATAAACGCT CAACGGGACC TTGAGTATTC CTCATTATCG         50

TTCTTCGACA TGAGGCCCGG ATC                                     73

(2) INFORMATION FOR SEQ ID NO:61:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:61:

GGGAGCTCAG AATAAACGCT CAAGTAGTGA AGCTCGTACA GAGGTATTGC         50

GTATTCGACA TGAGGCCCGG ATC                                     73

(2) INFORMATION FOR SEQ ID NO:62:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:62:

GGGAGCTCAG AATAAACGCT CAAAGCCGAA TTAGTAGCGT ATAGCGTGTT         50

GTGTTCGACA TGAGGCCCGG ATC                                     73

(2) INFORMATION FOR SEQ ID NO:63:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:63:

GGGAGCTCAG AATAAACGCT CAAGGGCAAT ACACAACACT CTACCTCACC         50

TCATTCGACA TGAGGCCCGG ATC                                     73

(2) INFORMATION FOR SEQ ID NO:64:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:64:

```
GGGAGCTCAG AATAAACGCT CAATCAGAGA TTCTTCCCGG CTATCCCGGG         50

TGATTCGACA TGAGGCCCGG ATC                                     73

(2) INFORMATION FOR SEQ ID NO:65:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:65:

GGGAGCTCAG AATAAACGCT CAATAGGCCG GGTGAGCTAC TTCTAGTAGG         50

GTGTTCGACA TGAGGCCCGG ATC                                     73

(2) INFORMATION FOR SEQ ID NO:66:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:66:

GGGAGCTCAG AATAAACGCT CAAGTTGTGA TCCATTAGCG GCACCGCCTC         50

CATTCGACAT GAGGCCCGGA TC                                      72

(2) INFORMATION FOR SEQ ID NO:67:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:67:

GGGAGCTCAG AATAAACGCT CAATCCGGAA AGCAACGCAT ACTTCGCATG         50

TCGTTCGACA TGAGGCCCGG ATC                                     73

(2) INFORMATION FOR SEQ ID NO:68:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:68:

GGGAGCTCAG AATAAACGCT CAAGTGAGCG TACCGGAGTG TGTTACCAAT         50

TATTCGACAT GAGGCCCGGA TC                                      72

(2) INFORMATION FOR SEQ ID NO:69:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:69:

GGGAGCTCAG AATAAACGCT CAACACATCT GCAGACTGTA CCCCACATGG         50

CAATTCGACA TGAGGCCCGG ATC                                     73
```

(2) INFORMATION FOR SEQ ID NO:70:

(i) SEQUENCE CHARACTERISTICS:
    (A) LENGTH: 73 base pairs
    (B) TYPE: nucleic acid
    (C) STRANDEDNESS: single
    (D) TOPOLOGY: linear (xi) SEQUENCE DESCRIPTION: SEQ ID NO:70:

```
GGGAGCTCAG AATAAACGCT CAAGAGGGCC GGGTTAGCCT TTTAAGGTTG        50

TGTTTCGACA TGAGGCCCGG ATC                                     73
```

(2) INFORMATION FOR SEQ ID NO:71:

(i) SEQUENCE CHARACTERISTICS:
    (A) LENGTH: 70 base pairs
    (B) TYPE: nucleic acid
    (C) STRANDEDNESS: single
    (D) TOPOLOGY: linear (xi) SEQUENCE DESCRIPTION: SEQ ID NO:71:

```
GCCTGTTGTG AGCCTCCTNN NNNNNNNNNN NNNNNNNNNN NNNNNNNNNN        50

NNGCCTTATT CTTGTCTCCC                                         70
```

(2) INFORMATION FOR SEQ ID NO:72:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:72:

```
GCCTGTTGTG AGCCTCCT                                           18
```

(2) INFORMATION FOR SEQ ID NO:73:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:73:

```
GGGAGACAAG AATAAGCG                                           18
```

(2) INFORMATION FOR SEQ ID NO:74:

(i) SEQUENCE CHARACTERISTICS:
    (A) LENGTH: 69 base pairs
    (B) TYPE: nucleic acid
    (C) STRANDEDNESS: single
    (D) TOPOLOGY: linear (xi) SEQUENCE DESCRIPTION: SEQ ID NO:74:

```
GCCTGTTGTG AGCCTCCTGG CTGCTGAGTC CAGGGGCGAT AACGGGCTTT        50

GCGCTTATTC TTGTCTCCC                                          69
```

(2) INFORMATION FOR SEQ ID NO:75:

(i) SEQUENCE CHARACTERISTICS:
    (A) LENGTH: 69 base pairs
    (B) TYPE: nucleic acid
    (C) STRANDEDNESS: single
    (D) TOPOLOGY: linear (xi) SEQUENCE DESCRIPTION: SEQ ID NO:75:

GCCTGTTGTG AGCCTCCTGG CTGCTGAGTC CAGGGGCGAT AACGGGCTTT        50

GCGCTTATTC TTGTCTCCC        69

(2) INFORMATION FOR SEQ ID NO:76:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:76:

GCCTGTTGTG AGCCTCCTGG CTGCTGAGTC CAGGGGCGAT AACGAGCTTT        50

CCGCTTATTC TTGTCTCCC        69

(2) INFORMATION FOR SEQ ID NO:77:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:77:

GCCTGTTGTG AGCCTCCTGG CTGCTGAGGC CAGGGGCGAT AACCGCACTT        50

TCGCTTATTC TTGTCTCCC        69

(2) INFORMATION FOR SEQ ID NO:78:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:78:

GCCTGTTGTG AGCCTCCTGG CTGCTGAGTC CAGGGGCGAT AACGGCCTTT        50

CCGCTTATTC TTGTCTCCC        69

(2) INFORMATION FOR SEQ ID NO:79:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:79:

GCCTGTTGTG AGCCTCCTTA GCGAACACAG GGGNCCACAA CTGGCTATCT        50

CTCGCTTATT CTTGTCTCCC        70

(2) INFORMATION FOR SEQ ID NO:80:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:80:

GCCTGTTGTG AGCCTCCTTA GCAGAACACA GGGGNCCACA ACTGGCTATC        50

```
TCCGCTTATT CTTGTCTCCC                                                    70

(2) INFORMATION FOR SEQ ID NO:81:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:81:

GCCTGTTGTG AGCCTCCTTA GGCGAACACA GGGGTCCACA ACTGGCTATC                   50

CCCGCTTATT CTTGTCTCCC                                                    70

(2) INFORMATION FOR SEQ ID NO:82:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:82:

GCCTGTTGTG AGCCTCCTTA GCGAACACAG GGTCAACAGC TCACACGGCC                   50

CGCTTATTCT TGTCTCCC                                                      68

(2) INFORMATION FOR SEQ ID NO:83:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:83:

GCCTGTTGTG AGCCTCCTTA GCGAACGARC GGTGCCCTGC TCTCAACTGG                   50

TTTCGCTTAT TCTTGTCTCC C                                                  71

(2) INFORMATION FOR SEQ ID NO:84:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:84:

GCCTGTTGTG AGCCTCCTTA GGCCGGAGGG ACTAATAGCT TACAGCGCAC                   50

TACGCTTATT CTTGTCTCCC                                                    70

(2) INFORMATION FOR SEQ ID NO:85:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:85:

GCCTGTTGTG AGCCTCCTTA GGCCGGAGGG ACTAATAGCT TACAAGGCAC                   50

TACGCTTATT CTTGTCTCCC                                                    70
```

```
(2) INFORMATION FOR SEQ ID NO:86:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:86:

GCCTGTTGTG AGCCTCCTTA GGAGCGCGAA CAACGGGGGA GGTCTCACAC            50

TGCGCTTATT CTTGTCTCCC                                             70

(2) INFORMATION FOR SEQ ID NO:87:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:87:

GCCTGTTGTG AGCCTCCTTA GGGGGNGNNA TACAACAGGT CGGTCACAAC            50

TGCGCTTATT CTTGTCTCCC                                             70

(2) INFORMATION FOR SEQ ID NO:88:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:88:

GCCTGTTGTG AGCCTCCTTA GGGCGGAGNG NGGCGGTCAT CCTGGNNACA            50

CTCCGCTTAT TCTTGTCTCC C                                           71

(2) INFORMATION FOR SEQ ID NO:89:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:89:

GCCTGTTGTG AGCCTCCTAG GCAGAAGTGA GCTTGGGCTC GCAACTCTCT            50

CCCGCTTATT CTTGTCTCCC                                             70

(2) INFORMATION FOR SEQ ID NO:90:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:90:

GCCTGTTGTG AGCCTCCTAG GCNGTAGGNG CTAGGGNGNA CTCGTATTCC            50

TCCGCTTATT CTTGTCTCCC                                             70

(2) INFORMATION FOR SEQ ID NO:91:

(i) SEQUENCE CHARACTERISTICS:
        (A) LENGTH: 70 base pairs
```

(B) TYPE: nucleic acid
            (C) STRANDEDNESS: single
            (D) TOPOLOGY: linear (xi) SEQUENCE DESCRIPTION: SEQ ID NO:91:

GCCTGTTGTG AGCCTCCTAG GCAGCAGTGA CTTGGACGAC AACAGCTATG          50

TCCGCTTATT CTTGTCTCCC                                          70

(2) INFORMATION FOR SEQ ID NO:92:

(i) SEQUENCE CHARACTERISTICS:
            (A) LENGTH:  70 base pairs
            (B) TYPE: nucleic acid
            (C) STRANDEDNESS: single
            (D) TOPOLOGY: linear (xi) SEQUENCE DESCRIPTION: SEQ ID NO:92:

GCCTGTTGTG AGCCTCCTAG GCAGTAGTGA CTTGGGCGCA GAGGAGGGTA          50

GTCGCTTATT CTTGTCTCCC                                          70

(2) INFORMATION FOR SEQ ID NO:93:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (xi) SEQUENCE DESCRIPTION: SEQ ID NO:93:

GCCTGTTGTG AGCCTCCTAG GGCGCAGGGT CTAGGGCANC CAACAGCTAT          50

TGCGCTTATT CTTGTCTCCC                                          70

(2) INFORMATION FOR SEQ ID NO:94:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (xi) SEQUENCE DESCRIPTION: SEQ ID NO:94:

GCCTGTTGTG AGCCTCCTAG GCGAAGGGNC TAGGGTGNAC AGCAGCGGTG          50

GCGCTTATTC TTGTCTCCC                                           69

(2) INFORMATION FOR SEQ ID NO:95:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (xi) SEQUENCE DESCRIPTION: SEQ ID NO:95:

GCCTGTTGTG AGCCTCCTNN NAGAGGGAAG ACTTTAGGTT CGGTTCACGT          50

CCCGCTTATT CTTGTCTCCC                                          70

(2) INFORMATION FOR SEQ ID NO:96:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (xi) SEQUENCE DESCRIPTION: SEQ ID NO:96:

GCCTGTTGTG AGCCTCCTNN NAGAGGGAAG ACTTAGGTTC GGTTCACGTC          50

CCGCTTATTC TTGTCTCCC                                            69

(2) INFORMATION FOR SEQ ID NO:97:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:97:

GCCTGTTGTG AGCCTCCTCC CAGAGGGAAG ACTTTAGGTT CGGTTCACGT          50

CCCCGCTTAT TCTTGTCTCC C                                         71

(2) INFORMATION FOR SEQ ID NO:98:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:98:

GCCTGTTGTG AGCCTCCTNC CAGAGGGNAG ACTTTAGGTT CGGTTCACGT          50

CCCGCTTATT CTTGTCTCCC                                           70

(2) INFORMATION FOR SEQ ID NO:99:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:99:

GCCTGTTGTG AGCCTCCTNN NAGAGGGAAG GCTTTAGGTT CGGTTCACGT          50

CCCGCTTATT CTTGTCTCCC                                           70

(2) INFORMATION FOR SEQ ID NO:100:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:100:

GCCTGTTGTG AGCCTCCTNN NAGAGGGAAG ACTTTAGGTT CGGTTCACGT          50

TCCGCTTATT CTTGTCTCCC                                           70

(2) INFORMATION FOR SEQ ID NO:101:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:101:

GCCTGTTGTG AGCCTCCTNN NAGAGGGNAG ACTTTAGGTT CGGTTCACGT          50

```
CCCGCTTATT CTTGTCTCCC                                                70

(2) INFORMATION FOR SEQ ID NO:102:

(i) SEQUENCE CHARACTERISTICS:
         (A) LENGTH: 71 base pairs
         (B) TYPE: nucleic acid
         (C) STRANDEDNESS: single
         (D) TOPOLOGY: linear (xi) SEQUENCE DESCRIPTION: SEQ ID NO:102:

GCCTGTTGTG AGCCTCCTGT GTGCAACAGA GCAGNNNTTG TCTAACATCA                50

CTTCGCTTAT TCTTGTCTCC C                                              71

(2) INFORMATION FOR SEQ ID NO:103:

(i) SEQUENCE CHARACTERISTICS:
         (A) LENGTH: 70 base pairs
         (B) TYPE: nucleic acid
         (C) STRANDEDNESS: single
         (D) TOPOLOGY: linear (xi) SEQUENCE DESCRIPTION: SEQ ID NO:103:

GCCTGTTGTG AGCCTCCTGG GGCGAACAGC AGCTACTCAC AACATGTCCG                50

GCCGCTTATT CTTGTCTCCC                                                70

(2) INFORMATION FOR SEQ ID NO:104:

(i) SEQUENCE CHARACTERISTICS:
         (A) LENGTH: 69 base pairs
         (B) TYPE: nucleic acid
         (C) STRANDEDNESS: single
         (D) TOPOLOGY: linear (xi) SEQUENCE DESCRIPTION: SEQ ID NO:104:

GCCTGTTGTG AGCCTCCTGT GGCGAACACG GGTCAAGGGC TTCACAATCT                50

GCGCTTATTC TTGTCTCCC                                                 69

(2) INFORMATION FOR SEQ ID NO:105:

(i) SEQUENCE CHARACTERISTICS:
         (A) LENGTH: 71 base pairs
         (B) TYPE: nucleic acid
         (C) STRANDEDNESS: single
         (D) TOPOLOGY: linear (xi) SEQUENCE DESCRIPTION: SEQ ID NO:105:

GCCTGTTGTG AGCCTCCTAT GGCGAACACA GCAACTCGCT CACAACTCTC                50

TCCCGCTTAT TCTTGTCTCC C                                              71

(2) INFORMATION FOR SEQ ID NO:106:

(i) SEQUENCE CHARACTERISTICS:
         (A) LENGTH: 70 base pairs
         (B) TYPE: nucleic acid
         (C) STRANDEDNESS: single
         (D) TOPOLOGY: linear (xi) SEQUENCE DESCRIPTION: SEQ ID NO:106:

GCCTGTTGTG AGCCTCCTGT AGGCGAACAC AGGTTGAGGC TTACACAGGG                50

NTCGCTTATT CTTGTCTCCC                                                70

(2) INFORMATION FOR SEQ ID NO:107:
```

(i) SEQUENCE CHARACTERISTICS:
    (A) LENGTH: 71 base pairs
    (B) TYPE: nucleic acid
    (C) STRANDEDNESS: single
    (D) TOPOLOGY: linear (xi) SEQUENCE DESCRIPTION: SEQ ID NO:107:

GCCTGTTGTG AGCCTCCTAG CGAACAACTG ACTGACGGCA GGGTCAACAC          50

NNCCGCTTAT TCTTGTCTCC C          71

(2) INFORMATION FOR SEQ ID NO:108:

(i) SEQUENCE CHARACTERISTICS:
    (A) LENGTH: 70 base pairs
    (B) TYPE: nucleic acid
    (C) STRANDEDNESS: single
    (D) TOPOLOGY: linear (xi) SEQUENCE DESCRIPTION: SEQ ID NO:108:

GCCTGTTGTG AGCCTCCTTA CGAACAACAG CATTCACACA GGCCTTTTTG          50

TTCGCTTATT CTTGTCTCCC          70

(2) INFORMATION FOR SEQ ID NO:109:

(i) SEQUENCE CHARACTERISTICS:
    (A) LENGTH: 70 base pairs
    (B) TYPE: nucleic acid
    (C) STRANDEDNESS: single
    (D) TOPOLOGY: linear (xi) SEQUENCE DESCRIPTION: SEQ ID NO:109:

GCCTGTTGTG AGCCTCCTAG CGAGCAACAT CTTTCGCAAC AGGTTTGGTT          50

CCCGCTTATT CTTGTCTCCC          70

(2) INFORMATION FOR SEQ ID NO:110:

(i) SEQUENCE CHARACTERISTICS:
    (A) LENGTH: 70 base pairs
    (B) TYPE: nucleic acid
    (C) STRANDEDNESS: single
    (D) TOPOLOGY: linear (xi) SEQUENCE DESCRIPTION: SEQ ID NO:110:

GCCTGTTGTG AGCCTCCTTT GGCGAACACA GCAACTCGCT CACAACTATC          50

TTCGCTTATT CTTGTCTCCC          70

(2) INFORMATION FOR SEQ ID NO:111:

(i) SEQUENCE CHARACTERISTICS:
    (A) LENGTH: 70 base pairs
    (B) TYPE: nucleic acid
    (C) STRANDEDNESS: single
    (D) TOPOLOGY: linear (xi) SEQUENCE DESCRIPTION: SEQ ID NO:111:

GCCTGTTGTG AGCCTCCTAG GTTGGGTAGG TTGGTGGAGG CGAACGTACC          50

AACGCTTATT CTTGTCTCCC          70

(2) INFORMATION FOR SEQ ID NO:112:

(i) SEQUENCE CHARACTERISTICS:
    (A) LENGTH: 70 base pairs
    (B) TYPE: nucleic acid (C) STRANDEDNESS: single
       (D) TOPOLOGY: linear (xi) SEQUENCE DESCRIPTION: SEQ ID NO:112:

GCCTGTTGTG AGCCTCCTAG GTTGGGTAGG TTGGTGGAGG CGAACGTCCT          50

AACGCTTATT CTTGTCTCCC                                           70

(2) INFORMATION FOR SEQ ID NO:113:

(i) SEQUENCE CHARACTERISTICS:
       (A) LENGTH: 70 base pairs
       (B) TYPE: nucleic acid
       (C) STRANDEDNESS: single
       (D) TOPOLOGY: linear (xi) SEQUENCE DESCRIPTION: SEQ ID NO:113:

GCCTGTTGTG AGCCTCCTAG GTTGGGTAGG CTGGTGGAGG CGNACGTCCC          50

ATCGCTTATT CTTGTCTCCC                                           70

(2) INFORMATION FOR SEQ ID NO:114:

(i) SEQUENCE CHARACTERISTICS:
       (A) LENGTH: 70 base pairs
       (B) TYPE: nucleic acid
       (C) STRANDEDNESS: single
       (D) TOPOLOGY: linear (xi) SEQUENCE DESCRIPTION: SEQ ID NO:114:

GCCTGTTGTG AGCCTCCTAG GTTCGCAGGC TGGCTGGAGG CGCGCGACCC          50

AACGCTTATT CTTGTCTCCC                                           70

(2) INFORMATION FOR SEQ ID NO:115:

(i) SEQUENCE CHARACTERISTICS:
       (A) LENGTH: 70 base pairs
       (B) TYPE: nucleic acid
       (C) STRANDEDNESS: single
       (D) TOPOLOGY: linear (xi) SEQUENCE DESCRIPTION: SEQ ID NO:115:

GCCTGTTGTG AGCCTCCTGG TTTGACCGTA ACAATTGTTA AAGCTCCGGG          50

NNCGCTTATT CTTGTCTCCC                                           70

(2) INFORMATION FOR SEQ ID NO:116:

(i) SEQUENCE CHARACTERISTICS:
       (A) LENGTH: 70 base pairs
       (B) TYPE: nucleic acid
       (C) STRANDEDNESS: single
       (D) TOPOLOGY: linear (xi) SEQUENCE DESCRIPTION: SEQ ID NO:116:

GCCTGTTGTG AGCCTCCTGG TCTGATCGTA ACAATTGTTA AAGCTCCGGG          50

NCCGCTTATT CTTGTCTCCC                                           70

(2) INFORMATION FOR SEQ ID NO:117:

(i) SEQUENCE CHARACTERISTICS:
       (A) LENGTH: 70 base pairs
       (B) TYPE: nucleic acid
       (C) STRANDEDNESS: single
       (D) TOPOLOGY: linear (xi) SEQUENCE DESCRIPTION: SEQ ID NO:117:

```
GCCTGTTGTG AGCCTCCTGG TTTGATCTCT AACAATTGTT AAAGCTCCAG        50

GCCGCTTATT CTTGTCTCCC                                         70

(2) INFORMATION FOR SEQ ID NO:118:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:118:

GCCTGTTGTG AGCCTCCTGG TCTGATCGCT AACAATTGTT AAAGCTCCGG        50

GGCCGCTTAT TCTTGTCTCC C                                       71

(2) INFORMATION FOR SEQ ID NO:119:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:119:

GCCTGTTGTG AGCCTCCTGG TCTGATCGTA ACAAATTGTT AAAAGCTCCG        50

GGCCCGCTTA TTCTTGTCTC CC                                      72

(2) INFORMATION FOR SEQ ID NO:120:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:120:

GCCTGTTGTG AGCCTCCTGG TTTGTCGTAA CAATTGTTAA AGCTCCGGGA        50

CCGCTTATTC TTGTCTCCC                                          69

(2) INFORMATION FOR SEQ ID NO:121:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:121:

GCCTGTTGTG AGCCTCCTGG TCTGATCGTA ACAGTTGTTA AAAGCTCCGG        50

GCGCGCTTAT TCTTGTCTCC C                                       71

(2) INFORMATION FOR SEQ ID NO:122:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:122:

GCCTGTTGTG AGCCTCCTGG TCTGATCGTA ACAATTGTTA AGCTCCGGGC        50

GCGCTTATTC TTGTCTCCC                                          69
```

(2) INFORMATION FOR SEQ ID NO:123:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:123:

```
GCCTGTTGTG AGCCTCCTCC GCCAAGGGAG CTCTCCGAGC TCGGCGCCAC          50

TCCGCTTATT CTTGTCTCCC                                           70
```

(2) INFORMATION FOR SEQ ID NO:124:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:124:

```
GCCTGTTGTG AGCCTCCTNC NNCNAAGGAA GATCTCCGAG TTCGGCGTCA          50

CTGCGCTTAT TCTTGTCTCC C                                         71
```

(2) INFORMATION FOR SEQ ID NO:125:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:125:

```
GCCTGTTGTG AGCCTCCTCT GCCGGGGAAG ATCTCCGAGT TCGGCGTCAC          50

TGCGCTTATT CTTGTCTCCC                                           70
```

(2) INFORMATION FOR SEQ ID NO:126:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:126:

```
GCCTGTTGTG AGCCTCCTCC GCCAAGGAAG ATCTCCGAGT TCGGCGTCAC          50

TGCGCTTATT CTTGTCTCCC                                           70
```

(2) INFORMATION FOR SEQ ID NO:127:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:127:

```
GCCTGTTGTG AGCCTCCTCN GCNAAGGAAG ATCTCCGAGT TCGGCGTCAC          50

TGCGCTTATT CTTGTCTCCC                                           70
```

(2) INFORMATION FOR SEQ ID NO:128:

(i) SEQUENCE CHARACTERISTICS:
    (A) LENGTH: 70 base pairs
    (B) TYPE: nucleic acid
    (C) STRANDEDNESS: single
    (D) TOPOLOGY: linear (xi) SEQUENCE DESCRIPTION: SEQ ID NO:128:

GCCTGTTGTG AGCCTCCTCN GCCAAGGAAG ATCTCCGAGT TCGGCGTCAC            50

TACGCTTATT CTTGTCTCCC                                             70

(2) INFORMATION FOR SEQ ID NO:129:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:129:

GCCTGTTGTG AGCCTCCTCN NCNAAGGAAG ATCTCCAGTT CGGCGTCACT            50

GCGCTTATTC TTGTCTCCC                                              69

(2) INFORMATION FOR SEQ ID NO:130:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:130:

GCCTGTTGTG AGCCTCCTCN GCNAAGGAAG ATCTCCGAGT TCGGNGTTAC            50

TGCGCTTATT CTTGTCTCCC                                             70

(2) INFORMATION FOR SEQ ID NO:131:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:131:

GCCTGTTGTG AGCCTCCTAG ACCGTAGGGT TCGGGAGCGA TAAACAGTCG            50

TTCGCTTATT CTTGTCTCCC                                             70

(2) INFORMATION FOR SEQ ID NO:132:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:132:

GCCTGTTGTG AGCCTCCTAG ACCGTAGGGG CTTGGGCCAT CAACTGGCGC            50

GGCGCTTATT CTTGTCTCCC                                             70

(2) INFORMATION FOR SEQ ID NO:133:

(i) SEQUENCE CHARACTERISTICS:
        (A) LENGTH: 72 base pairs
        (B) TYPE: nucleic acid
        (C) STRANDEDNESS: single (D) TOPOLOGY: linear (xi) SEQUENCE DESCRIPTION: SEQ ID NO:133:

GCCTGTTGTG AGCCTCCTAG ACGGTAGCGC CTTGAGTGAA TCAATCAGNA         50

GTAACGCTTA TTCTTGTCTC CC                                      72

(2) INFORMATION FOR SEQ ID NO:134:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:134:

GCCTGTTGTG AGCCTCCTAG ACCGTTGGGA CTATAGGCGA ACACCAGCTA         50

CCACGCTTAT TCTTGTCTCC C                                       71

(2) INFORMATION FOR SEQ ID NO:135:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:135:

GCCTGTTGTG AGCCTCCTAG ACGGTAGCCC TTAACGGCGA ACAACGCGTT         50

TCGCTTATTC TTGTCTCCC                                          69

(2) INFORMATION FOR SEQ ID NO:136:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:136:

GCCTGTTGTG AGCCTCCTAG ACTGTAGAGA CTTGATGGGT CGCAACCGTC         50

ACGCTTATTC TTGTCTCCC                                          69

(2) INFORMATION FOR SEQ ID NO:137:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:137:

GCCTGTTGTG AGCCTCCTAG ACTGTAGAGG CTAGGGTAAC AACGGCTCGT         50

TTCGCTTATT CTTGTCTCCC                                         70

(2) INFORMATION FOR SEQ ID NO:138:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:138:

```
GCCTGTTGTG AGCCTCCTAG ACTGTGAGAG ACTAGGCGAG AAACGGGGTT                50

CTCCGCTTAT TCTTGTCTCC C                                               71

(2) INFORMATION FOR SEQ ID NO:139:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:139:

GCCTGTTGTG AGCCTCCTAG ACTGTAGAGG CTAGGGCATC AACAGTTCTT                50

CCCGCTTATT CTTGTCTCCC                                                 70

(2) INFORMATION FOR SEQ ID NO:140:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:140:

GCCTGTTGTG AGCCTCCTAG ACTGGAGAGA CTAGGCGAGA ACCGGGGCGC                50

CGCTTATTCT TGTCTCCC                                                   68

(2) INFORMATION FOR SEQ ID NO:141:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:141:

GCCTGTTGTG AGCCTCCTAG AGAGGAGAAC TTATAGGAAA CAACGGTCGG                50

CCGCTTATTC TTGTCTCCC                                                  69

(2) INFORMATION FOR SEQ ID NO:142:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:142:

GCCTGTTGTG AGCCTCCTAG ACTGTAGAGG CTAGGGTAAC AACGGCTCGT                50

CTGCGCTTAT TCTTGTCTCC C                                               71

(2) INFORMATION FOR SEQ ID NO:143:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:143:

GCCTGTTGTG AGCCTCCTAG ACTGTTGAGA CTAACTGCGA ACAACTGCTG                50

TACGCTTATT CTTGTCTCCC                                                 70
```

(2) INFORMATION FOR SEQ ID NO:144:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:144:

```
GCCTGTTGTG AGCCTCCTAG AGCTGTTGAC ACTAACGCGA ACAACAACTG        50

TACGCTTATT CTTGTCTCCC                                         70
```

(2) INFORMATION FOR SEQ ID NO:145:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:145:

```
GCCTGTTGTG AGCCTCCTTG GAGGCGATAC TTGGCGAACA ACAGGGGCTG        50

TACGCTTATT CTTGTCTCCC                                         70
```

(2) INFORMATION FOR SEQ ID NO:146:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:146:

```
GCCTGTTGTG AGCCTCCTAT GCCGAACAAC AGTCTGAACA ACAGGTCTGT        50

ATCGCTTATT CTTGTCTCCC                                         70
```

(2) INFORMATION FOR SEQ ID NO:147:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:147:

```
GCCTGTTGTG AGCCTCCTTA GAGCGAATAC TTGGCGGAAC AACAGGGCTG        50

TACGCTTATT CTTGTCTCCC                                         70
```

(2) INFORMATION FOR SEQ ID NO:148:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:148:

```
GCCTGTTGTG AGCCTCCTGG ACTGTAGAGA CCAGTGGAAC AACAGATCGG        50

TACGCTTATT CTTGTCTCCC                                         70
```

(2) INFORMATION FOR SEQ ID NO:149:

(i) SEQUENCE CHARACTERISTICS:

```
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:149:

GCCTGTTGTG AGCCTCCTTG GAGGCGAATC TGGCGAGACA ACAGCTTTAT           50

CTCCGCTTAT TCTTGTCTCC C                                         71

(2) INFORMATION FOR SEQ ID NO:150:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:150:

GCCTGTTGTG AGCCTCCTTG GAGGCGAAGT CTGGCGAACA AGCGCTTTAT           50

CTCCGCTTAT TCTTGTCTCC C                                         71

(2) INFORMATION FOR SEQ ID NO:151:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:151:

GCCTGTTGTG AGCCTCCTTG GAGGCGAATC TGTCGAACAA CACGTTTATC           50

CCCGCTTATT CTTGTCTCCC                                           70

(2) INFORMATION FOR SEQ ID NO:152:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:152:

GCCTGTTGTG AGCCTCCTGT CGGAGNAAAC TATGTGTTTT AGAGCCATCC           50

CCGCTTATTC TTGTCTCCC                                            69

(2) INFORMATION FOR SEQ ID NO:153:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:153:

GCCTGTTGTG AGCCTCCTGT ACGGAGAAAA CTATGTGTTT TAGAGCCATC           50

CCCGCTTATT CTTGTCTCCC                                           70

(2) INFORMATION FOR SEQ ID NO:154:

(i) SEQUENCE CHARACTERISTICS:
        (A) LENGTH: 70 base pairs
        (B) TYPE: nucleic acid
        (C) STRANDEDNESS: single
        (D) TOPOLOGY: linear
```

(xi) SEQUENCE DESCRIPTION: SEQ ID NO:154:

GCCTGTTGTG AGCCTCCTGT ACGGCGCAAA CAATGTGTTT TAGAGCNACT          50

CCCGCTTATT CTTGTCTCCC                                           70

(2) INFORMATION FOR SEQ ID NO:155:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:155:

GCCTGTTGTG AGCCTCCTGT GTAGACTGCA GAGACTGCCA GTGATCTCTC          50

CCCGCTTATT CTTGTCTCCC                                           70

(2) INFORMATION FOR SEQ ID NO:156:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:156:

GCCTGTTGTG AGCCTCCTGT GTAGACTGCA GAGACTGCCA GTGCTCTCTC          50

CCCGCTTATT CTTGTCTCCC                                           70

(2) INFORMATION FOR SEQ ID NO:157:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:157:

GCCTGTTGTG AGCCTCCTTT GGGGCGAACA CAGGTTGAGG CTTACACAGG          50

GTTCGCTTAT TCTTGTCTCC C                                         71

(2) INFORMATION FOR SEQ ID NO:158:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:158:

GCCTGTTGTG AGCCTCCTAG TAGGCGNACA CAGGTTGAGG CTTACACAGG          50

GTTCGCTTAT TCTTGTCTCC C                                         71

(2) INFORMATION FOR SEQ ID NO:159:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:159:

GCCTGTTGTG AGCCTCCTGA ACAGGCNNNT TACCTCTGTG GCCGTTTATC          50

CCTCCGCTTA TTCTTGTCTC CC                                               72

(2) INFORMATION FOR SEQ ID NO:160:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:160:

GCCTGTTGTG AGCCTCCTCA GCCCNCCTTA CCTCTGTGCA GTTTATCCCT                 50

CTCGCTTATT CTTGTCTCCC                                                  70

(2) INFORMATION FOR SEQ ID NO:161:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:161:

GCCTGTTGTG AGCCTCCTAG ACATGGACAC TAGGGGACAC TGCAGCCAAC                 50

TTCGCTTATT CTTGTCTCCC                                                  70

(2) INFORMATION FOR SEQ ID NO:162:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:162:

GCCTGTTGTG AGCCTCCTAG ACAGGAGTGA CTTGGCAGCT NACAGACGCT                 50

TCCGCTTATT CTTGTCTCCC                                                  70

(2) INFORMATION FOR SEQ ID NO:163:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:163:

GCCTGTTGTG AGCCTCCTGA GACAGGACTG ACTTGGCAGC TCACAGCGCT                 50

TCCGCTTATT CTTGTCTCCC                                                  70

(2) INFORMATION FOR SEQ ID NO:164:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:164:

GCCTGTTGTG AGCCTCCTTA GTGGCGAACG ACAGACTCTC ACACACACAG                 50

GCTTGCGCTT ATTCTTGTCT CCC                                              73

(2) INFORMATION FOR SEQ ID NO:165:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:165:

```
GCCTGTTGTG AGCCTCCTTA AGTGGCGAAC GACAGCTCTC ACACACAGGC        50

TTGCGCTTAT TCTTGTCTCC C                                       71
```

(2) INFORMATION FOR SEQ ID NO:166:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:166:

```
GCCTGTTGTG AGCCTCCTTA GTTCCTTGCT TATTCTTGCT TCCCTTGTCT        50

GCGCTTATTC TTGTCTCCC                                          69
```

(2) INFORMATION FOR SEQ ID NO:167:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:167:

```
GCCTGTTGTG AGCCTCCTAG CACTGAGATA CGCTTATTCT TGTCTCCGGG        50

CTTGTCGCTT ATTCTTGTCT CCC                                     73
```

(2) INFORMATION FOR SEQ ID NO:168:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:168:

```
GCCTGTTGTG AGCCTCCTGA GGACGATCAA CAGCGACTTA TTCTCACAAC        50

TGCGCTTATT CTTGTCTCCC                                         70
```

(2) INFORMATION FOR SEQ ID NO:169:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:169:

```
GCCTGTTGTG AGCCTCCTTC CCGCTTATTC TTGTCTCAGC TTATTATTCT        50

TGTCGCTTAT TCTTGTCTCC C                                       71
```

(2) INFORMATION FOR SEQ ID NO:170:

(i) SEQUENCE CHARACTERISTICS:
        (A) LENGTH: 71 base pairs (B) TYPE: nucleic acid
        (C) STRANDEDNESS: single
        (D) TOPOLOGY: linear (xi) SEQUENCE DESCRIPTION: SEQ ID NO:170:

GCCTGTTGTG AGCCTCCTGT GGNNNAAATT CNCTTATTCT TGTCTCTCGT            50

GGTCGCTTAT TCTTGTCTCC C                                          71

(2) INFORMATION FOR SEQ ID NO:171:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:171:

GCCTGTTGTG AGCCTCCTAC CAGTACGATT ATTCTTGTCT CCCTGNNTTN            50

NNTCGCTTAT TCTTGTCTCC C                                          71

(2) INFORMATION FOR SEQ ID NO:172:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:172:

GCCTGTTGTG AGCCTCCTGG TGGTTGAGCT TATTCTTGTC TCGATTTGCA            50

CGTGTCGCTT ATTCTTGTCT CCC                                        73

(2) INFORMATION FOR SEQ ID NO:173:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:173:

GCCTGTTGTG AGCCTCCTAC CTTGCGGCTT ATTCTTGTCT CGCTTCTTCT            50

TGTCGCTTAT TCTTGTCTCC C                                          71

(2) INFORMATION FOR SEQ ID NO:174:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:174:

GCCTGTTGTG AGCCTCCTAG TTGTTGTCCG CGTTTCTTGT CTCCCTTTTC            50

CTCGCTTATT CTTGTCTCCC                                            70

(2) INFORMATION FOR SEQ ID NO:175:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:175:

GCCTGTTGTG AGCCTCCTTA GTCCCTTGCT TATTCTTGTC TTCCCTTGTC         50

TGCGCTTATT CTTGTCTCCC                                          70

(2) INFORMATION FOR SEQ ID NO:176:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:176:

GCCTGTTGTG AGCCTCCTAC CTTCCGGCTT ATTCTTGTTC TCTGCTTATT         50

CTTGTCGCTT ATTCTTGTCT CCC                                      73

(2) INFORMATION FOR SEQ ID NO:177:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:177:

GCCTGTTGTG AGCCTCCTGT CGCTTATTCT TGTCTCCCTC TTATTCTTGT         50

CCCCGCTTAT TCTTGTCTCC C                                        71

(2) INFORMATION FOR SEQ ID NO:178:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:178:

GCCTGTTGTG AGCCTCCTAG CACGAGATAC GCTTATTCTT GTCTCCGCGC         50

TTCTCGCTTA TTCTTGTCTC CC                                       72

(2) INFORMATION FOR SEQ ID NO:179:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:179:

GCCTGTTGTG AGCCTCCTTG TGTTGTTGTT CTTTGTGTCA TCCCTGTTCC         50

TCCGCTTATT CTTGTCTCCC                                          70

(2) INFORMATION FOR SEQ ID NO:180:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO:180:

GCCTGTTGTG AGCCTCCTTA GTGCCTGGGA CGCTTATTCT TGTCTCCGGG         50

```
GNCTACGCTT ATTCTTGTCT CCC                                                    73

(2) INFORMATION FOR SEQ ID NO:181:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:181:

GCCTGTTGTG AGCCTCCTGG AGGCGCTTGT GTCTTGTTCC CTTGTGTGTC                       50

TCCGCTTATT CTTGTCTCCC                                                        70

(2) INFORMATION FOR SEQ ID NO:182:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:182:

GCCTGTTGTG AGCCTCCTGT GGGGTTGTTG TCTTATTCTT GTCTCCGGCG                       50

CTTATTCTTG TCTCCC                                                            66

(2) INFORMATION FOR SEQ ID NO:183:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:183:

GCCTGTTGTG AGCCTCCTAG TCCCCGCTTA TTCTTGTCTC CCTTATCGCG                       50

CGCTTATTCT TGTCTCCC                                                          68

(2) INFORMATION FOR SEQ ID NO:184:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:184:

GCCTGTTGTG AGCCTCCTAC ACGCTTATTC TTGTCTCCAC TTATTCTTGT                       50

CGCTTATTCT TGTCTCCC                                                          68

(2) INFORMATION FOR SEQ ID NO:185:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:185:

GCCTGTTGTG AGCCTCCTGT TGTCGCTTAT TCTTGTCTCT GTCTGTTTTG                       50

TCCGCTTATT CTTGTCTCCC                                                        70

(2) INFORMATION FOR SEQ ID NO:186:
```

(i) SEQUENCE CHARACTERISTICS:
            (A) LENGTH: 74 base pairs
            (B) TYPE: nucleic acid
            (C) STRANDEDNESS: single
            (D) TOPOLOGY: linear (xi) SEQUENCE DESCRIPTION: SEQ ID NO:186:

GCCTGTTGTG AGCCTCCTAG AGTGGGGGGC GCTTATTCTT GTCTCCACTC        50

GCTTGTCGCT TATTCTTGTC TCCC        74

(2) INFORMATION FOR SEQ ID NO:187:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (xi) SEQUENCE DESCRIPTION: SEQ ID NO:187:

GCCTGTTGTG AGCCTCCTGA CACCCGCCGC GCTTATTGTT GTCTCCNNNC        50

TTTCCGCTTA TTCTTGTCTC CC        72

(2) INFORMATION FOR SEQ ID NO:188:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (xi) SEQUENCE DESCRIPTION: SEQ ID NO:188:

GCCTGTTGTG AGCCTCCTGT TGTCGCTTAT TCTTGTCTCC CATCCTCTAC        50

TCCGCTTATT CTTGTCTCCC        70

(2) INFORMATION FOR SEQ ID NO:189:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (xi) SEQUENCE DESCRIPTION: SEQ ID NO:189:

GCCTGTTGTG AGCCTCCTAG CCGTGTCCAG CTTATTCTTG TCTCCTNNCT        50

TCCGCTTATT CTTGTCTCCC        70

(2) INFORMATION FOR SEQ ID NO:190:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (xi) SEQUENCE DESCRIPTION: SEQ ID NO:190:

GCCTGTTGTG AGCCTCCTGG TTGTGTGACT TCTATTTGNN TTTCGTGTCC        50

CCGCTTATTC TTGTCTCCC        69

(2) INFORMATION FOR SEQ ID NO:191:

(i) SEQUENCE CHARACTERISTICS:
            (A) LENGTH: 71 base pairs
            (B) TYPE: nucleic acid (C) STRANDEDNESS: single
        (D) TOPOLOGY: linear (xi) SEQUENCE DESCRIPTION: SEQ ID NO:191:

GCCTGTTGTG AGCCTCCTGT CGCTGTGTAC CGTTTTTTTC TTGTTTGCCT        50

GTCCGCTTAT TCTTGTCTCC C        71

(2) INFORMATION FOR SEQ ID NO:192:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:192:

GCCTGTTGTG AGCCTCCTGG TAGGTCCTTT TCTGTCTTCC TTGTTCTCTC        50

GCCGCTTATT CTTGTCTCCC        70

(2) INFORMATION FOR SEQ ID NO:193:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:193:

GCCTGTTGTG AGCCTCCTTG TCTGTCCGTT CTTTTTGTCT GTGTTTTCCC        50

NCGCTTATTC TTGTCTCCC        69

(2) INFORMATION FOR SEQ ID NO:194:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:194:

GCCTGTTGTG AGCCTCCTGT ACCTGTTGTC AGCTTTTACC CTTCGTTCCT        50

CCGCTTATTC TTGTCTCCC        69

(2) INFORMATION FOR SEQ ID NO:195:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:195:

GCCTGTTGTG AGCCTCCTAG TCGCGATTCT ATTTTTCACT TTCTGTTGTT        50

GCCGCTTATT CTTGTCTCCC        70

(2) INFORMATION FOR SEQ ID NO:196:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:196:

```
GCCTGTTGTG AGCCTCCTGT TGCCGTATCC TTGTGGAGTT TTCGTTTCTC            50

CCCGCTTATT CTTGTCTCCC                                             70

(2) INFORMATION FOR SEQ ID NO:197:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:197:

GCCTGTTGTG AGCCTCCTGT TGGTCNGTTC CTTTCTCTGT TGTTCTCCTC            50

CGCTTATTCT TGTCTCCC                                               68

(2) INFORMATION FOR SEQ ID NO:198:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:198:

GCCTGTTGTG AGCCTCCTTA GTCCCGCGGC TTATTTTTGT CTCCGTTCCG            50

TTCGCTTATT CTTGTCTCCC                                             70

(2) INFORMATION FOR SEQ ID NO:199:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:199:

GCCTGTTGTG AGCCTCCTAG TCCCTCNNNN ATCCTTTTGT TGTCTTGCTG            50

TCCGCTTATT CTTGTCTCCC                                             70

(2) INFORMATION FOR SEQ ID NO:200:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:200:

GCCTGTTGTG AGCCTCCTTG TGTGTGTGTC GGTGGTTTTT TGTCTTCCTT            50

TTGCCGCTTA TTCTTGTCTC CC                                          72

(2) INFORMATION FOR SEQ ID NO:201:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:201:

GCCTGTTGTG AGCCTCCTGT GTCCGTTGTT CGCGTTTTGT GNCCTGTTTT            50

TCCCGCTTAT TCTTGTCTCC C                                           71
```

(2) INFORMATION FOR SEQ ID NO:202:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:202:

GCCTGTTGTG AGCCTCCTAG AAGCCTTGTC GTCTTTCCGT TCTTCTTGT          50

CCGCTTATTC TTGTCTCCC                                          69

(2) INFORMATION FOR SEQ ID NO:203:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:203:

GCCTGTTGTG AGCCTCCTAC CGGTAGGAGT CCGTTTTTGT TTGCACTATG         50

CCCGCTTATT CTTGTCTCCC                                         70

(2) INFORMATION FOR SEQ ID NO:204:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:204:

GCCTGTTGTG AGCCTCCTAC CCNACTGTGA TGTTCGTGTT TTGTTCCTCC         50

NCCGCTTATT CTTGTCTCCC                                         70

(2) INFORMATION FOR SEQ ID NO:205:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:205:

GCCTGTTGTG AGCCTCCTGG TCACACCAGT CACAGCACCT ACGTCCTGCC         50

CTCCGCTTAT TCTTGTCTCC C                                       71

(2) INFORMATION FOR SEQ ID NO:206:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:206:

GCCTGTTGTG AGCCTCCTGT AGTGGAACCG ACTAGCGGGG TGAAGACTCC         50

TCCGCTTATT CTTGTCTCCC                                         70

(2) INFORMATION FOR SEQ ID NO:207:

(i) SEQUENCE CHARACTERISTICS:
    (A) LENGTH: 68 base pairs
    (B) TYPE: nucleic acid
    (C) STRANDEDNESS: single
    (D) TOPOLOGY: linear (xi) SEQUENCE DESCRIPTION: SEQ ID NO:207:

GCCTGTTGTG AGCCTCCTTA GCCCACAGCA ATTTTAGTCT GAGTTCCGTC            50

CGCTTATTCT TGTCTCCC                                              68

(2) INFORMATION FOR SEQ ID NO:208:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:208:

GCCTGTTGTG AGCCTCCTAG GCTGCCGTAA GCTTTGGGAA TTGGCCTGCT            50

GCCGCTTATT CTTGTCTCCC                                            70

(2) INFORMATION FOR SEQ ID NO:209:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:209:

GCCTGTTGTG AGCCTCCTTG GAGGCGAATC TGGCGAACAA CAGCCTTATC            50

TCCGCTTATT CTTGTCTCCC                                            70

(2) INFORMATION FOR SEQ ID NO:210:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:210:

GCCTGTTGTG AGCCTCCTGA GGCTGTAGAG GCTGACTGCG CGCAGCTGCT            50

GTGCGCTTAT TCTTGTCTCC C                                          71

(2) INFORMATION FOR SEQ ID NO:211:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:211:

GCCTGTTGTG AGCCTCCTGA GGCGAGACAG GGTAGCACCT CACAACATGC            50

CGCTTATTCT TGTCTCCC                                              68

(2) INFORMATION FOR SEQ ID NO:212:

(i) SEQUENCE CHARACTERISTICS:
        (A) LENGTH: 71 base pairs
        (B) TYPE: nucleic acid
        (C) STRANDEDNESS: single (D) TOPOLOGY: linear (xi) SEQUENCE DESCRIPTION: SEQ ID NO:212:

GCCTGTTGTG AGCCTCCTTG GACTGGAGAG ACCTTAGGAG TCATAACTCT          50

CTCCGCTTAT TCTTGTCTCC C                                        71

(2) INFORMATION FOR SEQ ID NO:213:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:213:

GCCTGTTGTG AGCCTCCTGA CTGAAGAGCT CAGAGGCGAT ACAGGCCGCT          50

GTCGCTTATT CTTGTCTCCC                                          70

(2) INFORMATION FOR SEQ ID NO:214:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:214:

GCCTGTTGTG AGCCTCCTAA GACAGCAGTG GCTAGGGCGA TAACTGTCAC          50

CACCGCTTAT TCTTGTCTCC C                                        71

(2) INFORMATION FOR SEQ ID NO:215:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:215:

GCCTGTTGTG AGCCTCCTGA CCGCAGGGTT CGGGAGCGAT AAACTAGACC          50

TTCGCTTATT CTTGTCTCCC                                          70

(2) INFORMATION FOR SEQ ID NO:216:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:216:

GCCTGTTGTG AGCCTCCTCA TGCGGGTTTG TCCGGACCTC AGCAACAGCT          50

ACCGCTTATT CTTGTCTCCC                                          70

(2) INFORMATION FOR SEQ ID NO:217:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:217:

```
GCCTGTTGTG AGCCTCCTGA AGGCGNANAC AGGAGGAAAG GCTNACACCT              50

ATCCGCTTAT TCTTGTCTCC C                                            71
```

(2) INFORMATION FOR SEQ ID NO:218:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:218:

```
GCCTGTTGTG AGCCTCCTGA CTGTAGAGAC AGGACGTACA ATAGGCTCAC              50

TCCGCTTATT CTTGTCTCCC                                              70
```

(2) INFORMATION FOR SEQ ID NO:219:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:219:

```
GCCTGTTGTG AGCCTCCTGT TGCATTCCAG GACCGTTCTG TCNGTACCTC              50

GCGCCGCTTA TTCTTGTCTC CC                                           72
```

(2) INFORMATION FOR SEQ ID NO:220:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:220:

```
GCCTGTTGTG AGCCTCCTAT GGGGGCGAAC CTTTGCGCTC ACAACCTACC              50

TGCCGCTTAT TCTTGTCTCC C                                            71
```

(2) INFORMATION FOR SEQ ID NO:221:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:221:

```
GCCTGTTGTG AGCCTCCTGA ACGACGGGAC AGGGCTGAAA ACAGGCAGCT              50

ACCGCTTATT CTTGTCTCCC                                              70
```

(2) INFORMATION FOR SEQ ID NO:222:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:222:

```
GCCTGTTGTG AGCCTCCTTG CGCGGTGTTG CNCTTTGTTC TATTCTCCTG              50

TCCGCTTATT CTTGTCTCCC                                              70
```

(2) INFORMATION FOR SEQ ID NO:223:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:223:

GCCTGTTGTG AGCCTCCTTG AACCACAAGC CCCAACTAAC AACACCCTGC         50

CGCTTATTCT TGTCTCCC                                           68

(2) INFORMATION FOR SEQ ID NO:224:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:224:

GCCTGTTGTG AGCCTCCTAG GGTGAGATCC AGGGCGCGCT ACGTGCGTGT         50

CCGCTTATTC TTGTCTCCC                                          69

(2) INFORMATION FOR SEQ ID NO:225:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:225:

GCCTGTTGTG AGCCTCCTAC CGCGACTCTT TGCGTACTTC TTGGTCTTCC         50

GCCTCGCTTA TTCTTGTCTC CC                                      72

(2) INFORMATION FOR SEQ ID NO:226:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (xi) SEQUENCE DESCRIPTION: SEQ ID NO:226:

GCCTGTTGTG AGCCTCCTTG GGCGAAGGGT CTTGGACGAG GACAGGCGCC         50

GCTTATTCTT GTCTCCC                                            67

(2) INFORMATION FOR SEQ ID NO:227:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:227:

GCCTGTTGTG AGCCTCCTAG GTCACCGTTA TCTCTTCCTG TTGCTCTTTC         50

GCCGCTTATT CTTGTCTCCC                                         70

(2) INFORMATION FOR SEQ ID NO:228:

(i) SEQUENCE CHARACTERISTICS:

```
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:228:

GCCTGTTGTG AGCCTCCTAG TCAAACCCCT CTACGCTGTT GTTGATGTCT           50

CCCCGCTTAT TCTTGTCTCC C                                          71

(2) INFORMATION FOR SEQ ID NO:229:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:229:

GCCTGTTGTG AGCCTCCTTA GGCAGAACTC ACTAAAAGGT CCAACTGGTT           50

CCCGCTTATT CTTGTCTCCC                                            70

(2) INFORMATION FOR SEQ ID NO:230:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:230:

GCCTGTTGTG AGCCTCCTTG GACAGGACTC ACCTACAAGG CTTACAACGC           50

ATCGCTTATT CTTGTCTCCC                                            70

(2) INFORMATION FOR SEQ ID NO:231:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:231:

GCCTGTTGTG AGCCTCCTGT AGACTGTAGA GTTACGGCGC GACTACAACG           50

CTCGCTTATT CTTGTCTCCC                                            70

(2) INFORMATION FOR SEQ ID NO:232:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:232:

GCCTGTTGTG AGCCTCCTAG GCGGTAGCTA CTAACATATC ACAACATCTT           50

ACCGCTTATT CTTGTCTCCC                                            70

(2) INFORMATION FOR SEQ ID NO:233:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

(xi) SEQUENCE DESCRIPTION: SEQ ID NO:233:

GCCTGTTGTG AGCCTCCT                                              18

(2) INFORMATION FOR SEQ ID NO:234:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:234:

GGGAGACAAG AATAAGCG                                              18

(2) INFORMATION FOR SEQ ID NO:235:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:235:

GCCTGTTGTG AGCCTCCTNN NNNNNNNNNN NNNNNNNNNN NNNNNNNNNN            50

NNCGCTTATT CTTGTCTCCC                                            70

(2) INFORMATION FOR SEQ ID NO:236:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:236:

AACTCAGTAA TGCCAAGGTA ACGGTT                                     26

(2) INFORMATION FOR SEQ ID NO:237:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:237:

CGAATCGCAT TGCCCAACGT TGCCCAAGAT TCG                             33

(2) INFORMATION FOR SEQ ID NO:238:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:238:

CGCTCAATAG TTGCCCACCG TTGTCCAATT GAGCG                           35

(2) INFORMATION FOR SEQ ID NO:239:

(i) SEQUENCE CHARACTERISTICS:
        (A) LENGTH: 31 base pairs
        (B) TYPE: nucleic acid
        (C) STRANDEDNESS: single -continued

```
        (D) TOPOLOGY: linear (xi) SEQUENCE DESCRIPTION: SEQ ID NO:239:

GTCGAGGCAT TGCAACCTTT GGTCTTTCGA C                              31

(2) INFORMATION FOR SEQ ID NO:240:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (xi) SEQUENCE DESCRIPTION: SEQ ID NO:240:

GGGCAACCTT GAGTATTTCA TGCTTCGACA TGAGGCCCG                      39
```